United States Patent
Gillies et al.

(10) Patent No.: US 7,186,804 B2
(45) Date of Patent: Mar. 6, 2007

(54) IL-2 FUSION PROTEINS WITH MODULATED SELECTIVITY

(75) Inventors: Stephen D. Gillies, Carlisle, MA (US); Pascal A. Stein, Boston, MA (US); Kin-Ming Lo, Lexington, MA (US)

(73) Assignee: EMD Lexigen Research Center Corp., Billerica, MA (US)

( * ) Notice: Subject to any disclaimer, the term of this patent is extended or adjusted under 35 U.S.C. 154(b) by 778 days.

(21) Appl. No.: 10/310,719

(22) Filed: Dec. 4, 2002

(65) Prior Publication Data

US 2003/0166163 A1    Sep. 4, 2003

Related U.S. Application Data

(60) Provisional application No. 60/371,966, filed on Apr. 12, 2002, provisional application No. 60/337,113, filed on Dec. 4, 2001.

(51) Int. Cl.
*C12N 15/62* (2006.01)
*C07K 14/55* (2006.01)

(52) U.S. Cl. .................. 530/351; 530/402; 435/69.7
(58) Field of Classification Search ............ None
See application file for complete search history.

(56) References Cited

U.S. PATENT DOCUMENTS

| | | |
|---|---|---|
| 4,196,265 A | 4/1980 | Koprowski et al. |
| 4,469,797 A | 9/1984 | Albarella |
| 4,676,980 A | 6/1987 | Segal et al. |
| 4,703,008 A | 10/1987 | Lin |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |
| 5,728,552 A | 3/1998 | Fujisawa et al. |
| 5,733,876 A | 3/1998 | O'Reilly et al. |
| 5,756,349 A | 5/1998 | Lin |
| 5,756,461 A | 5/1998 | Stephens |
| 5,759,551 A | 6/1998 | Ladd et al. |
| 5,770,195 A | 6/1998 | Hudziak et al. |
| 5,800,810 A | 9/1998 | Doyle et al. |
| 5,807,715 A | 9/1998 | Morrison et al. |
| 5,827,516 A | 10/1998 | Urban et al. |
| 5,827,703 A | 10/1998 | Debs et al. |
| 5,837,682 A | 11/1998 | Folkman et al. |
| 5,837,821 A | 11/1998 | Wu |

(Continued)

FOREIGN PATENT DOCUMENTS

AU    21725/88    3/1989

(Continued)

OTHER PUBLICATIONS

Adkins et al., (1998, "Edrecolomab (Monoclonal Antibody 17-1A)," *Drugs*, 56(4):619-626.

(Continued)

*Primary Examiner*—Prema Mertz
(74) *Attorney, Agent, or Firm*—Kirkpatrick & Lockhart Nicholson Graham LLP

(57) ABSTRACT

The invention provides cytokine fusion proteins with an increased therapeutic index, and methods to increase the therapeutic index of such fusion proteins. The fusion proteins of the invention are able to bind to more than one type of cytokine receptor expressed on cells and also bind to more than one cell type. In addition, the fusion proteins of the invention exhibit a longer circulating half-life in a patient's body than the corresponding naturally occurring cytokine.

23 Claims, 2 Drawing Sheets

U.S. PATENT DOCUMENTS

| | | | |
|---|---|---|---|
| 5,843,423 A | 12/1998 | Lyman et al. | |
| 5,854,205 A | 12/1998 | O'Reilly et al. | |
| 5,856,298 A | 1/1999 | Strickland | |
| 5,858,347 A | 1/1999 | Bauer et al. | |
| 5,885,795 A | 3/1999 | O'Reilly et al. | |
| 5,886,178 A | 3/1999 | Allen et al. | |
| 5,888,772 A | 3/1999 | Okasinski et al. | |
| 5,888,773 A | 3/1999 | Jost et al. | |
| 5,891,680 A | 4/1999 | Lieschke et al. | |
| 5,908,626 A | 6/1999 | Chang et al. | |
| 5,922,685 A | 7/1999 | Rakhmilevich et al. | |
| 5,955,422 A | 9/1999 | Lin | |
| 5,994,104 A | 11/1999 | Anderson et al. | |
| 5,994,126 A | 11/1999 | Steinman et al. | |
| 6,080,409 A | 6/2000 | Laus et al. | |
| 6,086,875 A | 7/2000 | Blumberg et al. | |
| 6,100,387 A | 8/2000 | Herrmann et al. | |
| 6,169,070 B1 | 1/2001 | Chen et al. | |
| 6,171,588 B1 | 1/2001 | Carron et al. | |
| 6,231,536 B1 | 5/2001 | Lentz | |
| 6,277,375 B1 | 8/2001 | Ward | |
| 6,281,010 B1 | 8/2001 | Gao et al. | |
| 6,284,536 B1 | 9/2001 | Morrison et al. | |
| 6,291,158 B1 | 9/2001 | Winter et al. | |
| 6,335,176 B1 | 1/2002 | Inglese et al. | |
| 6,340,742 B1 | 1/2002 | Burg et al. | |
| 6,348,192 B1 | 2/2002 | Chan et al. | |
| 6,406,689 B1 | 6/2002 | Falkenberg et al. | |
| 6,429,199 B1 | 8/2002 | Krieg et al. | |
| 6,444,792 B1 | 9/2002 | Gray et al. | |
| 6,475,717 B1 | 11/2002 | Enssle et al. | |
| 6,485,726 B1 | 11/2002 | Blumberg et al. | |
| 6,500,641 B1 | 12/2002 | Chen et al. | |
| 6,506,405 B1 | 1/2003 | Desai et al. | |
| 6,551,592 B2 | 4/2003 | Lindhofer et al. | |
| 6,583,272 B1 | 6/2003 | Bailon | |
| 6,586,398 B1 | 7/2003 | Kinstler et al. | |
| 6,617,135 B1 | 9/2003 | Gillies et al. | |
| 6,620,413 B1 | 9/2003 | DeSauvage et al. | |
| 6,627,615 B1 | 9/2003 | Debs et al. | |
| 6,646,113 B1 | 11/2003 | Dreyfuss et al. | |
| 6,750,329 B1 | 6/2004 | Rosenblum et al. | |
| 6,838,260 B2 | 1/2005 | Gillies et al. | |
| 6,955,807 B1 * | 10/2005 | Shanafelt et al. | 424/85.2 |
| 2001/0053539 A1 | 12/2001 | Lauffer et al. | |
| 2002/0037558 A1 | 3/2002 | Lo et al. | |
| 2002/0081664 A1 | 6/2002 | Lo et al. | |
| 2002/0142374 A1 | 10/2002 | Gallo et al. | |
| 2002/0146388 A1 | 10/2002 | Gillies | |
| 2002/0147311 A1 | 10/2002 | Gillies et al. | |
| 2002/0192222 A1 | 12/2002 | Blumberg et al. | |
| 2002/0193570 A1 | 12/2002 | Gillies et al. | |
| 2003/0003529 A1 | 1/2003 | Bayer | |
| 2003/0012789 A1 | 1/2003 | Blumberg et al. | |
| 2003/0044423 A1 | 3/2003 | Gillies et al. | |
| 2003/0049227 A1 | 3/2003 | Gillies et al. | |
| 2003/0105294 A1 | 6/2003 | Gillies et al. | |
| 2003/0124678 A1 | 7/2003 | Epstein et al. | |
| 2003/0139365 A1 | 7/2003 | Lo et al. | |
| 2003/0139575 A1 | 7/2003 | Gillies | |
| 2003/0157054 A1 | 8/2003 | Gillies et al. | |
| 2003/0166163 A1 | 9/2003 | Gillies | |
| 2003/0166877 A1 | 9/2003 | Gillies et al. | |
| 2004/0013640 A1 | 1/2004 | Zardi et al. | |
| 2004/0033210 A1 | 2/2004 | Gillies | |
| 2004/0043457 A1 | 3/2004 | Schumacher et al. | |
| 2004/0053366 A1 | 3/2004 | Lo et al. | |
| 2004/0072299 A1 | 4/2004 | Gillies et al. | |
| 2004/0082039 A1 | 4/2004 | Gillies et al. | |
| 2004/0180035 A1 | 9/2004 | Gillies et al. | |
| 2004/0180386 A1 | 9/2004 | Carr et al. | |
| 2004/0203100 A1 | 10/2004 | Gillies et al. | |
| 2005/0069521 A1 | 3/2005 | Gillies et al. | |

FOREIGN PATENT DOCUMENTS

| | | |
|---|---|---|
| CN | 93100115.3 | 7/1993 |
| DE | 37 12985 | 11/1988 |
| DE | 37 12985 A1 | 11/1988 |
| EP | 0 158 198 A1 | 10/1985 |
| EP | 0 211 769 A2 | 2/1987 |
| EP | 0 237 019 A2 | 9/1987 |
| EP | 0 256 714 A2 | 2/1988 |
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 319 012 A2 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 519 596 A1 | 12/1992 |
| EP | 0 344 134 B1 | 1/1994 |
| EP | 0 601 043 B1 | 6/1994 |
| EP | 0 640 619 A1 | 3/1995 |
| EP | 0 668 353 A1 | 8/1995 |
| EP | 0 699 755 A2 | 3/1996 |
| EP | 0 428 596 B1 | 4/1996 |
| EP | 0 706 799 A2 | 4/1996 |
| EP | 0 790 309 A1 | 8/1997 |
| EP | 1 088 888 A1 | 4/2001 |
| GB | 2 188 638 | 10/1987 |
| GB | 2 292 382 A | 2/1996 |
| JP | 63-267278 | 11/1988 |
| JP | 63-267296 | 11/1988 |
| WO | WO 86/01533 | 3/1986 |
| WO | WO 88/00052 | 1/1988 |
| WO | WO 88/07089 | * 9/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 93/20185 | 10/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/08570 | 3/1996 |
| WO | WO 96/18412 | 6/1996 |
| WO | WO 96/31526 | 10/1996 |
| WO | WO 96/40792 | 12/1996 |
| WO | WO 97/00317 | 1/1997 |
| WO | WO 97/00319 | 1/1997 |
| WO | WO 97/15666 | 5/1997 |

| | | |
|---|---|---|
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO 98/52976 | 11/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 00/78334 A1 | 12/2000 |
| WO | WO 01/07081 A1 | 2/2001 |
| WO | WO 01/10912 A1 | 2/2001 |
| WO | WO 01/36489 | 5/2001 |
| WO | WO 01/58957 | 8/2001 |
| WO | WO 02/02143 | 1/2002 |
| WO | WO 02/066514 | 8/2002 |
| WO | WO 02/072605 | 9/2002 |
| WO | WO 02/079232 | 10/2002 |
| WO | WO 02/079415 | 10/2002 |
| WO | WO 02/090566 | 11/2002 |
| WO | WO 03/015697 A2 | 2/2003 |
| WO | WO 03/048334 | 6/2003 |
| WO | WO 03/077834 | 9/2003 |

OTHER PUBLICATIONS

Anderson et al., (1980), "Characterization of the Fc Receptor for IgG on a Human Macrophage Cell Line U937," *J. Immunol.*, 125(6):2735-41.

Anderson et al., (1994), "Effects of Route and Formulation on Clinical Pharmacokinetics of Interleukin-2," *Clin. Pharmacokinet.*, 27(1):19-31.

Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.

Batra et al., (1993), "Insertion of Constant Region Domains of Human IgG1 into CD4-PE40 Increases Its Plasma Half-Life," *Molecular Immunology*, 30(4):379-386.

Boulianne et al., (1984), "Production of Functional Chimaeric Mouse/Human Antibody," *Nature*, 312:643-6.

Bourgois et al., (1974), "Determination of the Primary Structure of a Mouse IgG2a Immunoglobulin: Amino- Acid Sequence of the Fc Fragment: Implications for the Evolution of Immunoglobulin Structure and Function," *Eur. J. Biochem.*, 43:423-35.

Brambell et al., (1964), "A Theoretical Model of γ-Globulin Catabolism," *Nature*, 203:1352-55.

Brekke et al., (1994), "Human IgG Isotype-Specific Amino Acid Residues Affecting Complement- Mediated Cell Lysis and Phagocytosis," *Eur. J. Immunol.*, 24:2542-2547.

Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," *J. Immunol.*, 148:92-98.

Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.

Cohen et al., (1998), "An Artificial Cell-Cycle Inhibitor Isolated from a Combinatorial Library," *Proc. Natl. Acad. Sci. USA*, 95:14272-7.

Cirulli et al., (1998), "KSA Antigen Ep-CAM Mediates Cell—Cell Adhesion of Pancreatic Epithelial Cells: Morphoregulatory Roles in Pancreatic Islet Development," *J. Cell Biol.*, 140:1519-34.

Ellison et al., (1982), "The Nucleotide Sequence of a Human Immunoglobulin C $\gamma_1$ Gene," *Nucleic Acids Res.*, 10:4071-9.

Farner et al., (1995), "Distinction Between $\gamma_c$ C Detection and Function in YT Lymphoid Cells and in the Granulocyte-Macrophage Colony-Stimulating Factor-Responsive Human Myeloid Cell Line, Tf-1," *Blood*, 86:4568-78.

Ghetie et al., (1997), "FcRn: The MHC Class I-Related Receptor that is More Than an IgG Transporter," *Immunology Today*, 18(12):592-598.

Gren et al., (1983), "A New Type of Leukocytic Interferon," English Translation of *Dokl. Akad. Nauk. SSSR.*, 269(4):986-990.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Halin et al., (2002), "Enhancement of the Antitumor Activity of Interleukin-12 by Targeted Delivery to Neovasculature," *Nature Biotechnology*, 20:264-269.

Holden et al., (2001), "Augementation of Antitumor Activity of an Antibody-Interleukin 2 Immunocytokine with Chemotherapeutic Agents," *Clinical Cancer Research*, 7:2862-2869.

Hori et al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.

Hu et al., (1996), "A Chimeric Lym- 1/Interleukin 2 Fusion Protein for Increasing Tumor Vascular Permeability and Enhancing Antibody Uptake," *Cancer Research*, 56:4998-5004.

Hulett et al., (1994), "Molecular Basis of Fc Receptor Function," *Adv. Immunol.*, 57:1127.

Huston et al., (1988), "Protein Engineering of Antibody Binding Sites: Recovery of Specific Activity in an Anti-Digoxin Single-Chain Fv Analogue Produced In *Escherichia coli*," *Proc. Natl. Acad. Sci. USA*, 85:5879-5883.

Isaacs et al., (1998), "Therapy with Monoclonal Antibodies. II. The Contribution of Fcγ Receptor Binding and the Influence of CH1 and CH3 Domains on In Vivo Effector Funcion," *J. Immunol.*, 161:3862-3869.

Jefferis et al., (1990), "Molcular Definition of Interaction Sites on Human 1gG for Fc Receptors huFcγR," *Mol. Immunol.*, 27(12):1237-1240.

Junghans et al., (1996), "The Protection Receptor of 1gG Catabolism is the B2-Microglobulin-Containing Neonatal Intestinal Transport Receptor," *Proc. Natl. Acad. Sci. USA*, 93(11):5512-5516.

Kelner et al., (1994), "Lymphotactin: A Cytokine that Represents a New Class of Chemokine," *Science*, 266:1395-9.

King et al., (2004), "Phase 1 Clinical Trial of the Immunocytokine EMD 273063 in Melanoma Patients," *J. Clin. Oncol.*, 22(22):4463-73.

Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lo et al., (1998), "High Level Expression and Secretion of Fc-X Fusion Proteins in Mammalian Cells," *Protein Engineering*, 11(6):495-500.

Lode et al., (1999), "Tumor-Targeted IL-2 Amplifies T Cell-Mediated Immune Response Induced by Gene Therapy with Single-Chain IL-12," *Proc. Natl. Acad. Sci. USA*, 96:8591-8596.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Martin et al., (2001), "Crystal Structure at 2.8 Å of an FcRn/Heterodimeric Fc Complex: Mechanism of pH-Dependent Binding," *Mol. Cell.*, 7(4):867-77.

Mateo et al., (2000), "Removal of Amphipathic Epitopes from Genetically Engineered Antibodies: Production of Modified Immunoglobulins with Reduced Immunogenicity," *Hybridoma*,19(6):463-471.

McMahan et al., (1991), "A Novel IL-1 Receptor, Cloned From B-Cells by Mammalian Expression is Expressed in Many Cell Types," *EMBO J.*, 10:2821-32.

Mènard et al., (1983), "Generation of Monoclonal Antibodies Reacting with Normal and Cancer Cells of Human Breast," *Cancer Res.*, 43:1295-300.

Miyake et al., (1988), "Synthesis of Recombinant Human Single-Chain Urokinase-Type Plasminogen Activator Variants Resistant to Plasmin and Thrombin," *J. Biochem.*, 104:643-647.

Morrison et al., (1984), "Chimeric Human Antibody Molecules: Mouse Antigen-Binding Domains with Human Constant Region Domains," *Proc. Natl. Acad. Sci. USA*, 81:6851-5.

Nastala et al., (1994), "Recombinant IL-12 Administration Induces Tumor Regression in Association with IFN-γ Production," *J. Immunol.*, 153:1697-706.

Neal et al., (2004), "Enhanced Activity of Hul4.18-IL2 Immunocytokine against Murine NXS2 Neuroblastoma when Combined with Interleukin-2 Therapy," *Clin. Cancer. Res.*, 10:4839-4847.

Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.

Orlandi et al., (1989), "Cloning Immunoglobulin Variable Domains for Expression by the Polymerase Chain Reaction," *Proc. Natl. Acad. Sci. USA*, 86:3833-7.

Pedley et al. (1999), "Enhancement of Antibody-Directed Enzyme Prodrug Therapy in Colorectal Xenografts by an Antivascular Agent," *Cancer Res.*, 59:3998-4003.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et al., (1989), "A Humanized Antibody that Binds to the Interleukin 2 Receptor," *Proc. Natl. Acad. Sci. USA*, 86:10029-33.

Riechmann et al., (1988), "Reshaping Human Antibodies for Therapy," *Nature*, 332:323-7.

Robinson et al., (1998), "Optimizing the Stability of Single-Chain Proteins by Linker Length and Composition Mutagenesis," *Proc. Natl. Acad. Sci. USA*, 95:5929-34.

Sakano et al., (1980), "Two Types of Somatic Recombination are Necessary for the Generation of Complete Immunoglobin Heavy-Chain Genes," *Nature*, 286:676-683.

Schwartzberg et al., (2001), "Clinical Experience with Edrecolomab: A Monoclonal Antibody Therapy for Colon Carcinoma," *Critical Reviews in Oncology/Hematology*, 40:17-24.

Senior et al., (2000), "Cleavage of a Recombinant Human Immunoglobulin A2 (igA2)-IgA1 Hybrid Antibody by Certain Bacterial 1gA1 Proteases," *Infect. Immun.*, 68(2):463-9.

Sharma et al., (1999), "T cell-Derived IL-10 Promotes Lung Cancer Growth by Suppressing Both T cell and APC Function," *Journal of Immunology*, 163:5020-5028.

Sharp et al., (1988), "Codon Usage Patterns in *Escherichia coli*, *Bacillus subtilis*, *Saccharomyces cerevisiae*, *Schizosaccharomyces pombe*, *Drosophila melanogaster* and *Homo sapiens*; a Review of the Considerable Within-Species Diversity," *Nucleic Acids Res.*, 16(17):8207-8211.

Takai, (2002), "Roles of Rc Receptors in Autoimmunity," *Nat. Rev. Immunol.*, 2(8):580-92.

Tiruppathi et al., (1996), "Isolation and Characterization of a Cell Surface Albumin-Binding Protein from Vascular Endothelial Cells," *Proc. Nat. Acad. Sci. USA*, 93:250-4.

Voest et al., (1995), "Inhibition of Angiogenesis in Vivo by Interleukin 12," *J. Natl. Canc. Inst.*, 87:581-6.

Ward et al., (1995), "The Effector Functions of Immunoglobulins: Implications for Therapy," *Therapeutic. Immunology*, 2:77-94.

Weitkamp et al., (1973), "Additional Data on the Population Distribution of Human Serum Albumin Genes; Three New Variants," *Ann. Hum. Genet.*, 37:219-26.

Wetzel et al., (2001), "BAY50-4798, an Interleukin-2 (IL-2) Variant, Demonstrates Selective Activation of Human and Chimpanzee T Cells Relative to NK Cells but Shows Less Selectivity for T Cells from Monkeys and Rodents," *ASCO 2001 Annual Meeting*, Abstract #1051.

Woof et al., (1986), "Localisation of the Monocyte-Binding Region on Human Immunoglobulin G," *Mol. Immunol.*, 23:319-30.

Wysocka et al., (1995), "Interleukin-12 is Required for Interferon-γ Production and Lethality in Lipopolysaccharide-Induced Shock in Mice," *Eur. J. Immunol.*, 25:672-6.

Yan et al., (1996), "Characterization of an 1g VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.

Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Conner et al., (2004), "Ex vivo Evaluation of Anti-EpCAM Immunocytokine huKS-IL2 in Ovarian Cancer," *J. Immunotherapy*, 27:211-219.

Cruse et al., (eds.), (1995), *Illustrated Dictionary of Immunology*, p. 158, CRC Press, NY.

de la Salle et al., (1996), "Fc-γR on Human Dendritic Cells," in *Human IgG Receptors*, pp. 39-55, van de Winkel et al. (eds.), R.G. Landes Co.

Dorai et al., (1991), "Aglycosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Elliott et al., (1996), "Fine-Structure Epitope Mapping of Antierythropoietin Monoclonal Antibodies Reveals a Model of Recombinant Human Erythropoietin Structure," *Blood*, 87(7):2702-2713.

Gillies et al., (1991), "Targeting Human Cytotoxic T Lymphocytes to Kill Heeterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Handgretinger et al., (1995), "A Phase 1 Study of Human/Mouse Chimeric Anti-ganglioside GD2 Antibody ch14.18 in Patients with Neuroblastoma," *European J. Cancer*, 31A(2):261-267.

Hurn et al., (1980), "Production of Reagent Antibodies," *Methods in Enzymology*, 70: 104-142.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Ko et al., (2004), "Safety, Pharmacokinetics, and Biological Pharmacodynamics of the Immunocytokine EMD 273066 (huKS-IL2)," *J. Immunotherapy*, 27:232-239.

Lo et al., (1992), "Expression and Secretion of an Assembled Tetrameric CH2-deleted Antibody in *E. Coli.,*" *Hum. Antibod. Hybridomas*, 3:123-128.

Maecker et al., (1997), "DNA Vaccination with Cytokine Fusion Constructs Biases the Immune Response to Ovalbumin," *Vaccine*, 15(15):1687-1696.

Mueller et al., (1990), "Enhancement of Antibody-Dependent Cytotoxicity With A Chimeric Anti-GD2 Antibody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Reisfeld et al., (1994), "Potential of Genetically Engineered Anti-Ganglioside GD2 Antibodies for Cancer Immunotherapy," *Prog. Brain Res.*, 101:201-212.

Saleh et al., (1992), "Phase 1 Trial of the Chimeric Anti-GD2 Monoclonal Antibody ch14.18 in Patients With Malignant Melanoma," *Hum. Antibod. Hybridomas*, 3:19-24.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.*, 179:1109-1118.

Schlom (1991), "Monoclonal Antibodies: They're More and Less Than You Think," in *Molecular Foundations of Oncology*, pp. 95-133.

Weber et al., (2001), "Phase 1 Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.

Wen et al., (1994), "Erythropoietin Structure-Function Relationships: Identification of Functionally Important Domains," *J. Biological Chemistry*, 269(36):22839-22846.

Angal et al., (1993), "A Single Amino Acid Substitution Abolishes the Heterogeneity of Chimeric Mouse/Human (IgG4) Antibody," *Molecular Immunology*, 30(1):105-108.

Becker et al., (1996), "Long-lived and Transferable Tumor Immunity in Mice after Targeted Interleukin-2 Therapy," *J. Clin. Invest.*, 98(12):2801-2804.

Becker et al., (1996), "T Cell-mediated Eradication of Murine Metastatic Melanoma Induced by Targeted Interleukin-2 Therapy," *J. Exp. Med.*, 183(50):2361-2366.

Bitonti et al., (2002), "Transepithelial Absorption of an Erythropoietin-Fc Fusion Protein After Delivery to the Central Airways," *Respiratory Drug Delivery*, 8:309-312.

Briggs et al., (1974), "Hepatic Clearance of Intact and Desialylated Erythropoietin," *American Journal of Physiology*, 227(6):1385-1388.

Chuang et al., (1994), "Alteration of Lymphocyte Microtubule Assembly, Cytotoxicity, and Activation by the Anticancer Drug Taxol," *Cancer Research*, 54:1286-1291.

Cruse et al., (eds.), (1995), *Illustrated Dictionary of Immunology*, pp. 156-157, CRC Press, NY.

Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: Amplification of Anticancer Immunity," *Cancer Immunol. Immunother.*, 52:297-308.

Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.

Duncan et al., (1988), "The Binding Site for C1q on IgG," *Nature*, 332:738-740.

Egrie et al., (2001), "Development and Characterization of Novel Erythropoiesis Stimulating Protein (NESP)," *Nephrol. Dial. Transplant.*, 16(Supp 3):3-13.

Elliott et al., (1997), "Mapping of the Active Site of Recombinant Human Erythropoietin," *Blood*, 89(2):493-502.

Fibi et al., (1995), "N- and O-Glycosylation Muteins of Recombinant Human Erythropoietin Secreted From BHK-21 Cells," *Blood*, 85(5):1229-1236.

Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.

Gan et al., (1999), "Specific Enzyme-linked Immunosorbent Assays for Quantitation of Antibody-cytokine Fusion Proteins," *Clinical and Diagnostic Laboratory Immunology*, 6(2):236-42.

Gillies et al., (1991), "Expression of Genetically Engineered Immunoconjugates of Lymphotoxin and a Chimeric Anti-ganglioside GD2 Antibody," *Hybridoma.*, 10(3):347-56.

Gillies et al., (2002), "Bi-functional Cytokine Fusion Proteins for Gene Therapy and Antibody-targeted Treatment of Cancer," *Cancer Immunol. Immunother.*, 51(8):449-60.

Gillies et al., (2002), "Improved Circulating Half-life and Efficacy of an Antibody-interleukin 2 Immunocytokine Based on Reduced Intracellular Proteolysis," *Clin. Cancer Research*, 8(1):210-216.

Greene et al., (1975), "Neuronal Properties of Hybrid Neuroblastoma X Sympathetic Ganglion Cells," *Proc. Natl. Acad. Sci. USA*, 72(12):4923-4927.

Hammerling et al., (1996), "In Vitro Bioassay for Human Erythropoietin Based on Proliferative Stimulation of an Erythroid Cell Line and Analysis of Carbohydrate-dependent Microheterogeneity," *Journal of Pharmaceutical and Biomedical Analysis*, 14:1455-1469.

Hank et al., (1996), "Activation of Human Effector Cells by a Tumor Reactive Recombinant Anti-ganglioside GD2 Interleukin-2 Fusion Protein (ch14.18-IL2)," *Clin Cancer Research*, 2(12):1951-1959.

Hank et al., (2003), "Determination of Peak Serum Levels and Immune Response to the Humanized Anti-ganglioside Antibody-interleukin-2 Immunocytokine," in *Methods in Molecular Medicine*, vol. 85: *Novel Anticancer Drug Protocols*, Buolamwini et al., (eds.), pp. 123-131, Humana Press Inc., Totowana, NJ.

Haraguchi, (1994), "Isolation of GD3 Synthase Gene by Expression Cloning of GM3 α-2,8-sialyltransferase cDNA using anti-GD2 Monoclonal Antibody," *Proc. Natl. Acad. Sci. USA*, 91(22):10455-10459.

Harris, (1995), "Processing of C-terminal Lysine and Arginine Residues of Proteins Isolated from Mammalian Cell Culture," *J. Chromatography A*, 705:129-134.

Hezareh et al., (2001), "Effector Function Activities of a Panel of Mutants of a Broadly Neutralizing Antibody against Human Immunodeficiency Virus Type 1," *J. Virology*, 75(24):12161-12168.

Idusogie et al., (2000), "Mapping of the C1q Binding Site on Rituxan, a Chimeric Antibody with a Human IgG1 Fc," *J. Immunology*, 164(8):4178-4184.

Imboden et al., (2001), "The Level of MHC Class I Expression on Murine Adenocarcinoma Can Change the Antitumor Effector Mechanism of Immunocytokine Therapy," *Cancer Research*, 61(4):1500-7.

Kato et al., (1997), "Mechanism for the Nonlinear Pharmacokinetics of Erythropoietin in Rats," *The Journal of Pharmacology and Experimental Therapeutics*, 283:520-527.

Kato et al., (1998), "Pharmacokinetics of Erythopoietin in Genetically Anemic Mice," *Drug Metabolism and Disposition*, 26(2):126-131.

Kitamura et al., (1989), "Establishment and Characterization of a Unique Human Cell Line that Proliferates Dependently on GM-CSF, IL-3, or Erythropoietin," *Journal of Cellular Physiology*, 140:323-334.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

Locatelli et al., (2001), "Darbepoetin alfa Amgen," *Current Opinion in Investigational Drugs*, 2:1097-1104.

Lode et al., (1997), "Targeted Interleukin-2 Therapy for Spontaneous Neuroblastoma Metastases to Bone Marrow," *J. Natl. Cancer Inst.*, 89(21):1586-94.

Lode et al., (2000), "What To Do With Targeted IL-2," *Drugs of Today*, 36(5):321-336.

Lode et al., (2000), "Melanoma Immunotherapy by Targeted IL-2 Depends on CD4(+)T-cell Help Mediated by CD40/CD40L Interaction," *J. Clin. Invest.*, 105(11):1623-30.

Macdougall, (2002), "Optimizing the Use of Erythropoietic Agents—Pharmacokinetic and Pharmacodynamic Considerations," *Nephrol. Dial. Transplant.*, 17(Supp 5):66-70.

Metelitsa et al., (2002), "Antidisialoganglioside/granulocyte Macrophage-colony-stimulating Factor Fusion Protein Facilitates Neutrophil Antibody-dependent Cellular Cytotoxicity and Depends on FcγRII (CD32) and Mac-1 (CDI1b/CD18) for Enhanced Effector Cell Adhesion and Azurophil Granule Exocytosis," *Blood*, 99(11):4166-73.

Mueller et al., (1997), "Humanized Porcine VCAM-specific Monoclonal Antibodies with Chimeric IgG2/G4 Constant Regions Block Human Leukocyte Binding to Porcine Endothelial Cells," *Molecular Immunology*, 34(6):441-452.

Mullins et al., (1997), "Taxol-mediated Changes in Fibrosarcoma-induced Immune Cell Function: Modulation of Antitumor Activities," *Cancer Immunol. Immunother*, 45:20-28.

Naramura et al., (1994), "Mechanisms of Cellular Cytotoxicity Mediated by a Recombinant Antibody-IL2 Fusion Protein Against Human Melanoma Cells," *Immunology Letters*, 39:91-99.

Neal et al., (2003), "NXS2 Murine Neuroblastomas Express Increased Levels of MHC Class I Antigens upon Recurrence Following NK-dependent Immunotherapy," *Cancer Immunol. Immunother.*, 53:41-52.

Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2002) "An Oral DNA Vaccine Against Human Carcinoembryonic Antigen (CEA) Prevents Growth and Dissemination of Lewis Lung Carcinoma in CEA Transgenic Mice," *Vaccine*, 20:421-429.

Niethammer et al., (2001) "Targeted Interleukin 2 Therapy Enhances Protective Immunity Induced by an Autologous Oral DNA Vaccine against Murine Melanoma," *Cancer Research*, 61(16):6178-84.

Nimtz et al., (1993), "Structures of Sialylated Oligosaccharides of Human Erythropoietin Expressed in Recombinant BHK-21 Cells," *Eur. J. Biochem.*, 213:39-56.

Pancook et al., (1996), "Eradication of Established Hepatic Human Neuroblastoma Metastases in Mice with Severe Combined Immunodeficiency by Antibody-targeted Interleukin-2," *Cancer Immunol. Immunother.*, 42(2):88-92.

Park et al., (2000), "Efficiency of Promoter and Cell Line in High-level Expression of Erythropoietin," *Biotechnol. Appl. Biochem.*, 32:167-172.

Reisfeld et al., (1996), "Antibody-interleukin 2 Fusion Proteins: A New Approach to Cancer Therapy," *J. Clin. Lab Anal.*, 10:160-166.

Reisfeld et al., (1996), "Involvement of B Lymphocytes in the Growth Inhibition of Human Pulmonary Melanoma Metastases in Athymic *nu/nu* Mice by an Antibody-lymphotoxin Fusion Protein," *Cancer Research*, 56(8):1707-1712.

Ruehlmann et al., (2001), "MIG (CIXCL9) Chemokine Gene Therapy Combines with Antibody-cytokine Fusion Protein to Suppress Growth and Dissemination of Murine Colon Carcinoma," *Cancer Research*, 61(23):8498-503.

Sabzevari et al., (1994), "A Recombinant Antibody-interleukin 2 Fusion Protein Suppresses Growth of Hepatic Human Severe Combined Immunodeficiency Mice," *Proc. Natl. Acad. Sci. USA*, 91(20):9626-30.

Seidenfeld et al., (2001), "Epoietin Treatment of Anemia Associated with Cancer Therapy: A Systematic Review and Meta-analyis of Controlled Clinical Trials," *Journal of National Cancer Institute*, 93(16):1204-1214.

Shinkawa et al., (2003), "The Absence of Fucose But Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, 278:3466-3473.

Spiekermann et al., (2002), "Receptor-mediated Immunoglobulin G Transport Across Mucosal Barriers in Adult Life: Functional Expression of FcRn in the Mammalian Lung," *J. Exp. Med.*, 196:303-310.

Strom et al., (1996), "Therapeutic Approach to Organ Transplantation," Chapter 36, pp. 451-456, in *Therapeutic Immunology*, Austen et al., (eds.), Blackwell Science.

Syed et al., (1998), "Efficiency of Signaling Through Cytokine Receptors Depends Critically on Receptor Orientation," *Nature*, 395:511-516.

Thommesen et al., (2000), "Lysine 322 in the Human IgG3 CH2 Domain is Crucial for Antibody Dependent Complement Activation," *Mol. Immunol.*, 37(16):995-1004.

Wells, (1990), "Additivity of Mutational Effect in Proteins," *Biochemistry*, 29(37):8509-8517.

Xiang et al., (1998), "Induction of Persistent Tumor-protective Immunity in Mice Cured of Established Colon Carcinoma Metastases," *Cancer Research*, 58(17):3918-3925.

Xiang et al., (1999) "T Cell Memory against Colon Carcinoma is Long-lived in the Absence of Antigen," *J. Immunology*, 163(7):3676-83.

Xiang et al., (2001), "A Dual Function DNA Vaccine Encoding Carcinoembryonic Antigen and CD40 Ligand Trimer Induces T Cell-mediated Protective Immunity Against Colon Cancer in Carcinoembryonic Antigen-Transgenic Mice," *J. Immunology*, 167(8):4560-5.

Xiang et al., (2001), "Protective Immunity Against Human Carcinoembryonic Antigen (CEA) Induced by an Oral DNA Vaccine in CEA-transgenic Mice," *Clinical Cancer Research*, 7(3 Supp):S856-S864.

Yu et al., (1998), "Phase 1 Trial of a Human-Mouse Chimeric Anti-Disaloganglioside Monoclonal Antibody ch14.18 in Patients with Refractory Neuroblastoma and Osteosarcoma," *J. Clinical Oncology*, 16(6):2169-80.

Zagozdzon et al., (1999), "Potentiation of Antitumor Effects of IL-12 in Combination with Paclitaxel in Murine Melanoma Model In Vivo," *International Journal of Molecular Medicine*, 4:645-648.

U.S. Appl. No. 07/348,237, filed May 5, 1989, Rosenblum et al.

Abaza et al., (1992), "Effects of Amino Acid Substitutions Outside an Antigenic Site on Protein Binding to Monoclonal Antibodies of Predetermined Specificity Obtained by Peptide Immunization," *Journal of Protein Chemistry*, 11:5:433-444.

Abstract XP-002116766. (1996). "Prostaglandins. their inhibitors and cancer," *Prostaglandins, Leukotrienes and Essential Fatty Acids*, 54:2:83-94.

Afonso et al., (1994), "The Adjuvant Effect of Interleukin-12 in a Vaccine Against Leishmania Major," *Science*, 263:235-237.

Arenberg et al. (1996), "Interferon-γ-inducible Protein 10 (IP-10) Is an Angiostatic Factor That Inhibits Human Non-small Cell Lung Cancer (NSCLC) Tumorigenesis and Spontaneous Metastases," *J. Exp. Med*, 184:981-992.

Bacha et al., (1988), "Interleukin 2 Receptor-Targeted Cytotoxicity Interleukin 2 Receptor-mediated Action of a Diphtheria Toxin-related Interleukin 2 Fusion Protein," *J. Experimental Medicine*, 167:612-622.

Bachelot et al., (Mar. 1998), "Retrovirus-Mediated Gene Transfer of an Angiostatin-Endostatin Fusion protein with Enhanced Anti-Tumor Properties In Vivo," *Proceedings of the Annual Meeting of the American Association for Cancer Research*, 39:271, Abstract #1856.

Barnett et al., (1994), "Purification, characterization and selective inhibition of human prostaglandin G/H synthase 1 and 2 expressed in the baculovirus system," *Biochimica et Biophysica Acta*, 1209:130-139.

Baselga, et al., (1998), "Recombinant Humanized Anti-HER2 Antibody (Herceptin™) Enhances the Antitumor activity of Paclitaxel and Doxorubicin against HER3/neu Overexpressing Human Breast Cancer Xenografts," *Cancer Research*, 58:2825-2831.

Batova et al., (1999), "The Ch 14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263.

Batra et al., (1993), "Insertion of Constant Region Domains of Human IgG1 into CD4-PE40 Increases Its Plasma Half-Life," *Mol. Immunol.*, 30:379-386.

Becker et al., (1996), "An Antibody-Interleukin 2 Fusion Protein Overcomes Tumor Heterogeneity by Induction of a Cellular Immune Response," *Proc. Natl. Acad. Sci.*, 93:7826-7831.

Becker et al., (1996), "Eradication of human hepatic and pulmonary melanoma metastases in SCID mice by antibody-interleukin 2 fusion proteins," *Proc. Natl. Acad. Sci. USA*, 93:2702-2707.

Beutler et al., (1988), "Tumor Necrosis, Cachexia, Shock, and Inflammation: A Common Mediator," *Ann. Rev. Biochem.*, 57:505-518.

Bissery et al., (1997), "The Taxoids," in *Cancer Therapeutics: Experimental and Clinical Agents*, Teicher, ed., 175-193.

Bjorn et al., (1985), "Evaluation of Monoclonal Antibodies for the Development of Breast Cancer Immunotoxins," *Cancer Research*, 45:1214-1221.

Boehm et al., (1997), "Antiangiogenic therapy of experimental cancer does not induce acquired drug resistance," *Nature*, 390:404-407.

Boehm et al., (1998), "Zinc-Binding of Endostatin Is Essential for Its Antiangiogenic Activity," *Biochemical and Biophysical Research Communications*, 252:190-194.

Boissel et al., (1993), "Erythropoietin Structure-Function Relationships," *The Journal of Biological Chemistry*, 268:15983-15993.

Brooks et al., (1994), "Integrin $\alpha_v\beta_3$ Antagonists Promote Tumor Regression by Inducing Apoptosis of Angiogenic Blood Vessels," *Cell*, 79:1157-1164.

Buchli et al., (1993), "Structural and Biologic Properties of a Human Aspartic Acid-126 Interleukin-2 Analog," *Archives of Biochemistry and Biophysics*, 307:2:411-415.

Burgess et al., (1990), "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology*, 111:2129-2138.

Canfield et al., (1991), "The Binding Affinity of Human IgG for its High Affinity Fc Receptor is Determined by Multiple Amino Acids in the CH2 Domain and Is Modulated by the Hinge Region," *Journal of Experimental Medicine*, 173:6:1483-1491.

Cao et al., (1996), "Kringle Domains of Human Angiostatin," *The Journal of Biological Chemistry*, 271:46:29461-29467.

Cao et al., (1997), "Kringle 5 of Plasminogen is a Novel Inhibitor of Endothelial Cell Growth," *The Journal of Biological Chemistry*, 272:36:22924-22928.

Capon et al., (1989), "Designing CD4 immunoadhesins for AIDS therapy," *Nature*, 337:525-531.

Caton et al., (1986), "Structural and functional implications of a restricted antibody response to a defined antigenic region on the influenza virus hemagglutinin," *The EMBO Journal*, 5:7:1577-1587.

Chan et al., (1991), "Induction of Interferon γ Production by Natural Killer Cell Stimulatory Factor: Characterization of the Responder Cells and Synergy with Other Inducers," *J. Exp. Med.*, pp. 869-879.

Chang et al., (1989), "Overview of Interleukin-2 as an Immunotherapeutic Agent," *Seminars in Surgical Oncology*, 5:385-390.

Chang et al., (1996), "A Point Mutation in Interleukin-2 that Alters Ligand Internalization," *Journal of Biological Chemistry*, 271:13349-13355.

Chaudhary et al., (1988), "Selective killing of HIV-infected cells by recombinant human CD4-Pseudomonas exotoxin hybrid protein," *Nature*, 335:370-372.

Chaudhary et al., (1989), "A recombinant immunotoxin consisting of two antibody variable domains fused to Pseudomonas exotoxin," *Nature*, 339:394-397.

Chen et al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," *Journal of Immunology*, 159:1:351-358.

Cheon et al., (1994), "High-affinity binding sites for related fibroblast growth factor ligands reside within different receptor immunoglobulin-like domains," *Proc. Natl. Acad. Sci. USA*, 91:989-993.

Chuang et al., (1993), "Effect of new investigational drug taxol on oncolytic activity and stimulation of human lymphocytes," *Gynecol. Oncol.*, 49:291-298.

Cohen, S. L. et al., (1996), "Human leptin characterization," *Nature*, 382:589.

Cole et al., (1997), "Human IgG2 Variants of Chimeric Anti-CD3 Are Nonmitogenic to T Cells," *Journal of Immunology*, 159:3613-3621.

Collins et al., (1988), "Identification of Specific Residues of Human Interleukin 2 that Affect Binding to the 70-kDa Subunit (p. 70) of the Interleukin 2 Receptor," *Proc. Natl. Acad. Sci*, 85:7709-7713.

Colombo et al., (1996), "Amount of Interleukin 12 Available at the Tumor Site is Critical for Tumor Regression," *Cancer Research*, 56:2531-2534.

D'Amato et al., (1994), "Thalidomide is an inhibitor of angiogenesis," *Proc. Natl. Acad. Sci. USA*, 91:4082-4085.

D'Andrea et al., (1992), "Production of Natural Killer Cell Stimulatory Factor (Interleukin 12) by Peripheral Blood Mononuclear Cells," *J. Exp. Med.*, 176:1387-1398.

Ding et al., (1988), "Zinc-Dependent Dimers Observed in Crystals of Human Endostatin," *Proceedings of the National Academy of Sciences of USA*, 95:10443-10448.

Earnest et al., (1992), "Piroxicam and Other Cyclooxygenase Inhibitors: Potential for Cancer Chemoprevention," *J. Cell. Biochem, Supp*, 161:156-166.

Eisenthal, (1990), "Indomethacin up-regulated the generation of lymphokine-activated killer-cell activity and antibody-dependent cellular cytotoxicity mediated by interleukin-2," *Cancer Immunol. Immunotherap.* 31:342-348.

Fell et al., (1991), "Genetic Construction and Characterization of Fusion Protein Consisting of a Chimeric F(ab') with Specificity for Carcinomas and Human IL-32," *The J. of Immunology*, 146:7:2446-2452.

Fell et al., (1992), "Chimeric L6 antitumor antibody," *The J. Biol. Chem.*, 267:15552-15558.

Friedman, J. M. et al., (1998), "Leptin and the regulation of body weight in mammals," *Nature*, 395:763-770.

Gasson et al., (1984), "Purified Human Granulocyte Macrophage Colony-Stimulating Factor: Direct Action on Neutrophils," *Science*, 226:1339-1342.

Gately et al., (1998), "The Interleukin-12/Interleukin-12 Receptor system: Role in Normal and Pathologic Immune Responses," *Annu. Rev. Immunol.*, 16:495-521.

Gillessen et al., (1995), "Mouse Interleukin-12 (IL-12) p40 Homodimer: A Potent IL-12 Antagonist," *Eur. J. Immunol.*, 25:200-206.

Gillies et al., (1989), "Expression of Human Anti-Tetanus Toxoid Antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen binding and biological activities of engineered mutant chimeric antibodies with human tumor specificities," *Hum. Antibod. Hybridomas*, 1:1:47-54.

Gillies et al., (1992), "Antibody-Targeted Interleukin 2 Stimulates T-Cell Killing of Autologous Tumor Cells," *Proc. Natl. Acad. Science*, 89:1428-1432.

Gillies et al., (1993), "Biological Activity and In Vivo Clearance of Antitumor Antibody/Cytokine Fusion Proteins," *Bioconjugate Chem.*, 4:230-235.

Gillies et al., (1998), "Antibody-IL-12 fusion proteins are effective in SCID mouse models of prostate and colon carcinoma matastases," *J. Immunology*, 160:2:6195-6203.

Gillies et al., (1999), "Improving the Efficacy of Antibody-Interleukin 2 Fusion Proteins by Reducing Their Interaction with Fc Receptors," *Cancer Research*, 59:2159-2166.

Gillis et al., (1978), "T Cell Growth Factor: Parameters of Production And A Quantitative Microassay for Activity," *Journal of Immunology*, 120:6:2027-2032.

Goeddel et al., (1986), "Tumor Necrosis Factors: Gene Structure and Biological Activities," *Pharm. Sciences*, pp. 597-609.

Gren et al., (1983), "A New Type of Leukocytic Interferon," *Dokl. Biochem.*, 269:91-95.

Griffon-Etienne et al., (1999), "Taxane-induced apoptosis decompresses blood vessels and lowers interstitial fluid pressure in solid tumors: clinical implications," *Cancer Research*, 59:3776-3782.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73:8:2081-2805.

Guyre et al., (1997), "Increased potency of Fc-receptor-targeted antigens," *Cancer Immunol. Immunother.*, 45:146-148.

Harris et al., (1993), "Therapeutic Antibodies—the Coming of Age," *Tibtech*, 11:42-44.

Harvill et al., (1995), "An IgG3-IL2 Fusion Protein Activates Complement, Binds FcYRI, Generates LAK Activity and Shows Enhanced Binding to the High Affinity IL-2R," *Immunotech.*, 1:95-105.

Harvill et al., (1996), "In vivo properties of an IgG3-IL-2 fusion protein: A general strategy for immune potentiation," *Journal of Immunology*, 157:7:3165-3170.

Hazama et al., (1993), "Adjuvant-Independent Enhanced Immune Responses to recombinant Herpes Simplex Virus Type 1 Glycoprotein D by Fusion with Biologically Active Interleukin-2," *Vaccine*:11;6:629-636.

He et al., (1998), "Humanization and Pharmacokinetics of Monoclonal Antibody with Specificity for Both E-and P-Selectin," *J. Immunol.*, 1029-1035.

Heijnen et al., (1996), "Antigen Targeting to Myeloid-specific Human FcYRI/CD64 Triggers Enhanced Antibody Responses in Transgenic Mice," *J. Clin. Invest.*, 97:2:331-338.

Heinzel et al., (1997), "In Vivo Production and Function of IL-12 p40 Homodimers," *J. Immunol.*, 158:4381-4388.

Hellstrom et al., (1986), "Antitumor effects of L6, an IgG2a antibody that reacts with most human carcinomas," *Proc. Natl. Acad. Sci.*, 83:18: 7059-7063.

Henkart, (1985), "Mechanism of Lymphocyte-Mediated Cytotoxicity," *Ann. Rev. Immunol.*, 3:31-58.

Herrmann et al., (1989), "Hematopoeitic Responses With Advanced Malignancy Treated With Recombinant Human Granulocyte-Macrophage Colony-Stimulating Factor," *Journal of Clinical Oncology*, 7:2 159-167.

Hohenester et al., (1998), "Crystal Structure of the Angiogenesis Inhibitor Endostatin at 1.5 Å Resolution," *EMBO Journal*, 17:6:1656-1664.

Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675.

Holden et al., (2001), "Augmentation of Antitumor activity of an Antibody-Interleukin 2 Immunocytokine with Chemotherapeutic Agents," *Clinical Cancer Research*, 7:2862-2869.

Hoogenboom et al., (1991), "Construction and expression of antibody-tumor necrosis factor fusion proteins," *Molecular Immunology*, 28:9:1027-1037.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. and Biophys. Acta*, 1096:4:345-354 (Abstract).

Hornick et al, (1999), "Pretreatment with a monoclonal antibody/interleukin-2 fusion protein directed against DNA enhances the delivery of therapeutic molecules to solid tumors," *Clin. Cancer Res.*, 5:51-60.

Hu et al., (1996), "A Chimeric Lym-1/Interleukin 2 Fusion Protein for Increasing Tumor Vascular Permeability and Enhancing Antibody Uptake[1]," *Cancer Research*, 56:4998-5004.

Huck et al., (1986), "Sequence of a human immunoglobulin gamma 3 heavy chain constant region gene: comparison with the other human Cγ genes," *Nucleic Acids Research*, vol. 14:4:1779-1789.

Huse et al., (1989), "Generation of a Large Combinatorial Library of the Immunoglobulin Repertoire in Phage Larnbda," *Science*, 246:1275-1281.

Ingber et al., (1990), "Synthetic analogues of fumagillin that inhibit angiogenesis and suppress tumour growth," *Nature*, 348:555-557.

Jones et al., (1986), "Replacing the complementarity-determining regions in a human antibody with those from a mouse," *Nature*, 321:6069.522-525.

Ju et al., (1987), "Structure-Function Analysis of Human Interleukin-2," *Journal of Biological Chemistry*, 262:12:5723-5731.

Jung et al, (1987), "Activation of human peripheral blood mononuclear cells by anti-T3: Killing of tumor target cells coated with anti-target-anti-T3 conjugates," *Proc. Natl. Acad. Sci.*, 83:4479-4483.

Junghans et al., (1996), "The protection receptor of IgG catabolism is the B2-micorgobulin-containing neonatal intestinal transport receptor," *Proc. Natl. Acad. Sci.*, 93:11:5512-5516.

Kang et al., (1991), "Antibody redesign by chain shuffling from random combinatorial immunoglobulin libraries," *Proc. Natl. Acad. Sci.*, 88:11120-11123.

Kappel et al., (1992), "Regulating gene expression in transgenic animals," *Current Opinion in Biotechnology* 3:548-553.

Karpovsky et al., (1984), "Production of Target-Specific Effector Cells using Hetero-Cross Linked Aggregate Containing Anti-Target Cell and AntiFcλ Receptor Antibodies," *Journal of Experimental Medicine*, 160:6:1686-1701.

Kendra et al., (1999), "Pharmacokinetics and Stability of the ch 14.18-Interleukin-2 Fusion Protein in Mice," *Cancer Immunol. Immunotherapy*, 48:219-229.

Kim et al., (1997), "An Ovalbumin-IL-12 fusion protein is more effective than ovalbumin plus free recombinant IL-12 in inducing a T helper cell type 1-dominated immune response and inhibiting antigen-specific IgE production," *Journal Immunology*, 158:9:4137-4144.

Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.

Kranz et al., (1984), "Attachment of an anti-receptor antibody to non-target cells renders them susceptible to lysis by a clone of cytotoxic T lymphocytes," *Proc. Natl. Acad. Sci.*, 81:7922-7926.

Kuo et al., (2001), "Oligomerization-dependent Regulation of Motility and Morphogenesis by the Collagen XVIII NC1/Endostatin Domain," *Journal of Cell Biology*, 152:6:1233-1246.

LaVaillie et al., (1993), "Cloning and Functional Expression of a cDNA Encoding the Catalytic Subunit of Bovine Enterokinase," *Journal of Biological Chemistry*, 268:31:23311-23317.

Lazar et al., (1988), "Transforming Growth Factor α: Mutation of Aspartic Acid 47 and Leucine 48 Results in Different Biological Activities," *Molecular and Cellular Biology*, 8:3:1247-1252.

LeBerthon et al., (1991), "Enhanced Tumor Uptake of Macromolecules Induced by a Novel Vasoactive Interleukin 2 Immunoconjugate," *Cancer Research*, 51:2694-2698.

Lieschke, et al., (1997), "Bioactive murine and human interleukin-12 fusion proteins which retain antitumor activity in vivo," *Nature Biotechnology*, 15:1:35-40.

Linsley et al., (1991), "CTLA-4 is a Second Receptor for B Cell Activation Antigen B7," *Journal of Experimental Medicine*, 174:3:561-569.

Liu et al., (1985), "Heteroantibody Duplexes Target Cells for Lysis by Cytotoxic T Lymphocytes, " *Proc. Natl. Acad. Sci.*, 82:8648-8652.

Liu et al., (1988), "Hormone Conjugated with Antibody to CD3 Mediates Cytotoxic T Cell Lysis of Human Melanoma Cells," *Science*, 239:395-398.

Liu et al., (1998), "Immunostimulatory CpG Oligodeoxynucleotides Enhance the Immune Response to Vaccine Strategies Involving Granulocyte-Macrophage Colony-Stimulating Factor," *Blood*, 92:10:3730-3736.

Lo et al., (1998), "High Level Expression and Secretion of Fc-X Fusion Proteins in Mammalian Cells," *Protein Engineering*, 11:6:495-500.

Lode et al., (1998), "Immunocytokines: a promising approach to cancer immunotherapy," *Pharmacol. Thera.*, 80:3:277-292.

Lode et al., (1998). "Natural Killer Cell-Mediated Eradication of Neuroblastoma Metastases to Bone Marrow by Targeted Interleukin-2 Therapy," *Blood*, 91:5:1706-1715.

Lode et al., (1999), "Synergy between an antiangiogenic integrin $\alpha_v$ antagonist and an antibody-cytokine fusion protein eradicates spontaneous tumor metastases," *Proc. Natl. Acad. Sci.*, 96:1591-1596.

Lode et al., (1999), "Tumor-targeted IL-2 amplifies T cell-mediated immune response induced by gene therapy with single-chain IL-12," *Proc. Natl. Acad. Sci.*, 96:8591-8596.

Lode et al., (2000), "Amplification of T Cell Mediated Immune Responses by Antibody-Cytokine Fusion Proteins," *Immunological Investigations*, 29:2:117-120.

Maloney et al., (1994), "Phase 1 Clinical Trial Using Escalating Single-Dose Infusion of Chimeric Anti-CD20 Monoclonal Antibody (IDEC-C2B8) in Patients with Recurrent B-Cell Lymphoma," *Blood*, 84:8:2457-2466.

Mark et al., (1992) "Expression and characterization of hepatocyte growth factor receptor-IgG fusion proteins," *Journal of Biological Chemistry*, 267:36:26166-26171.

Martinotti et al., (1995), "CD4 T Cells Inhibit in vivo the CD8-Mediated Immune Response Against Murine Colon Carcinoma Cells Transduced with Interleukin-12 Genes," *Eur. J. Immunol.* 25:137-146.

Medesan et al., (1997), "Delineation of the Amino Acid Residues Involved in Transcytosis and Catabolism of Mouse $1gG1^1$," *J. Immunology*, 158:5:2211-2217.

Mestre et al., (1997), "Retinoids Suppress Epidermal Growth Factor-induced Transcription of Cyclooxygenase-2 in Human Oral Squamous Carcinoma Cells," *Cancer Research*, 57:2890-2895.

Mosmann et al., (1989), "TH1 and TH2 CELLS: Different Patterns of Lymphokine Secretion Lead to Different Functional Properties," *Ann. Rev. Immunol*, 7:145-173.

Mott et al., (1995), "The Solution Structures of the F42A Mutant of Human Interleukin 2," *J. Mol. Biol.* 247:979-994.

Mullins et al., (1998), "Interleukin-12 overcomes paclitaxel-mediated suppression of T-cell proliferation" *Immunopharmacol. Immunotoxicol.*, 20:4:473-492.

Murphy et al., (1986), "Genetic construction, expression, and melanoma-selective cytotoxicity of a diphtheria toxin-related α-melanocyte-stimulating hormone fusion protein," *Proc. Natl. Acad. Sci.*, 83:8258-8262.

Murphy, (1988), "Diphtheria-related peptide hormone gene fusions: A molecular gene approach to chimeric toxin development," *Immunotoxins*, 123-140.

Nedwin et al., (1985), "Human Lymphotoxin and Tumor Necrosis Factor Genes: Structure, Homology and Chromosomal Localization," *Nucleic Acids Research*, 13:17:6361-6373.

Netti et al., (1995), "Time-dependent behavior of interstitial fluid pressure in solid tumors: implications for drug delivery," *Cancer Research*, 55:5451-5458.

Netti et al., (1999), "Enhancement of fluid filtration across tumor vessels: implication for delivery of macromolecules," *Proc. Nat. Acad. Sci*, 96:3137-3142.

Neuberger et al., (1984), "Recombinant Antibodies Possessing Novel Effector Functions." *Nature*, 312:604-608.

O'Reilly et al., (1994), "Angiostatin: A Novel Angiogenesis Inhibitor That Mediates the Suppression of Metastases by a Lewis Lung Carcinoma," *Cell*, 79:315-328.

O'Reilly et al., (1996), "Angiostatin induces and sustains dormancy of human primary tumors in mice," *Nature Medicine*, 2:6:689-692.

O'Reilly et al., (1997), "Endostatin: An Endogenous Inhibitor of Angiogenesis and Tumor Growth," *Cell*, 88:277-285.

Pastan et al., (1989), "Pseudomonas Exotoxin: Chimeric Toxins," *Journal of Biological Chemistry*, 264:26:15157-15160.

Paul et al., (1988), "Lymphotoxin," *Ann. Rev. Immunol.*, 6:407-438.

Perez et al., (1986), "Specific Targeting of Human Peripheral Blood T Cells by Heteroaggregates Containing Anti-T3 Crosslinked to Anti-Target cell antibodies," *J. Exp. Medicine*, 163:166-178.

Perez et al., (1989). "Isolation and Characterization of a cDNA Encoding the KS1/4 Epithelial Carcinoma Marker," *Journal of Immunology*, 142:10:3662-3667.

Polizzi et al., (1999), "A novel taxane with improved tolerability and therapeutic activity in a panel of human tumor xenografts," *Cancer Research*, 59:1036-1040.

Putzer et al., (1997), "Interleukin 12 and B7-1 Costimulatory Molecule Expressed by an Adenovirus Vector Act Synergistically to Facilitate Tumor Regression," *Proc. Nat'l Acad. Sci.*, 94:20:10889-10894.

Reisfeld et al., (1996), "Recombinant antibody fusion proteins for cancer immunotherapy," *Current Topics in Microbiology and Immunology*, 27-53.

Reisfeld et al., (1997), "Immunocytokines: a new approach to immunotherapy of melanoma." *Melanoma Research*, 7:2:S99-S106.

Riethmuller et al., (1994), "Randomised trial of monoclonal antibody for adjuvant therapy of resected Dukes' C colorectal carcinoma," *The Lancet*, 343:1177-1183.

Roessler et al., (1994), "Cooperative interactions between the interleukin 2 receptor α and β chains alter the interleukin 2-binding affinity of the receptor subunits," *Proc. Natl. Acad. Sci.*, 91:3344-3347.

Roitt et al., (1993), "The Role of TH Cells in the Selection of Effector Mechanisms Directed Against Target Antigens," *Immunology*, Third Edition, 8.3-8.4.

Rosenberg, (1988), "Immunotherapy of Cancer Using Interleukin 2: current status and future prospects," *Immunology Today*, 9:2:58-62.

Rozwarski et al., (1994), "Structural comparisons among the short-chain helical cytokines," *Structure*, 2:3:159-173.

Santon et al., (1986). "Effects of Epidermal Growth Factor Receptor Concentration on Tumorigenicity of A431 Cells in Nude Mice," *Cancer Research*, 46:4701-4705.

Sasaki et al., (1998), "Structure, function and tissue forms of the C-terminal globular domain of collagen XVII containing the angiogenesis inhibitor endostatin," *The EMBO Journal*, 17:15:4249-4256.

Sauve et al., (1991), "Localization in human interleukin 2 of the binding site of the α chain (p55) of the interleukin 2 receptor," *Proc. Natl. Acad. Sci.*, 88:4636-4640.

Schnee et al., (1987), "Construction and expression of a recombinant antibody-targeted plasminogen activator," *Proc. Natl. Acad. Sci.*, 84:6904-6908.

Schoenhaut et al., (1992), "Cloning and Expression of Murine IL-12," *Journal of Immunology*, 148:11:3433-3340.

Senter et al., (1988), "Anti-tumor effects of antibody-alkaline phosphatase conjugates in combination with etoposide phosphate," *Proc. Natl. Acad. Sci.*, 85:13:4842-4846.

Shanafelt et al., (2000), "A T-cell-selective interleukin 2 mutein exhibits potent antitumor activity and is well tolerated in vivo," *Nature Biotechnology*, 18:1197-1202.

Sharma et al., (1999), "T cell-derived IL-10 promotes lung cancer growth by suppressing both T cell and APC function," *Journal of Immunology*, 163:5020-5028.

Shen et al., (1986), "Heteroantibody-Mediated Cytotoxicity: Antibody to the high affinity Fc receptor for IgG mediates cytotoxicity by human monocytes that is enhanced by interferon-λ and is not blocked by human IgG," *Journal of Immunology*, 137:11:3378-3382.

Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.

Shin et al., (1990), "Expression and characterization of an antibody binding specificity joined to insulin-like growth factor 1: Potential applications for cellular targeting," *Proc. Natl. Acad. Sci.*, 87:5322-5326.

Sim et al., (1997), "A Recombinant Human Angiostatin Protein Inhibits Experimental Primary Metastatic Cancer," *Cancer Research*, 57:1329-1334.

Stevenson et al., (1997), "Conjugation of Human Fcγ in Closed-Hinge or Open-Hinge Configuration to Fab'γ and Analogous Ligands," *Journal of Immunology*, 158:2242-2250.

Sulitzeanu et al., (1993), "Immunosuppressive factors in human cancer," *Adv. Cancer Research*, 60:247-267.

Taniguchi et al., (1983), "Structure and expression of a cloned cDNA for human interleukin-2," *Nature*, 302:305-309.

Tao et al., (1989), "Studies of Aglycosylated Chimeric Mouse IgG: Role of Carbohydrate in the Structure and Effector Functions Mediated by the Human IgG Constant Region," *Journal of Immunology*, 143:8:2595-2601.

Tao et al., (1993), "Structural Features of Human Immunoglobulin G that Determine Isotype-Differences in Complement Activation," *Journal of Experimental Medicine*, 178:2:661-667.

Teicher et al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 990-993, 1278-1283 (17th ed. 1999).

Till et al., (1988), "An Assay that Predicts the Ability of Monoclonal Antibodies to Form Potent Ricin A Chain-containing Immunotoxins," *Cancer Research*, 48:5:1119-1123.

Till et al., (1988), "HIV-Infected Cells are Killed by rCD4-Ricin A Chain," *Science*, 242:1166-1168.

Trinchieri, (1994), "Interleukin-12: A Cytokine Produced by Antigen-Presenting Cells With Immunoregulatory Functions in the Generaton of T-Helper Cells Type 1 and Cytotoxic Lymphocytes," *Blood*, 84:4008-4027.

Vagliani et al., (1996), "Interleukin 12 Potentiates the Curative Effect of a Vaccine Based on Interleukin 2-transduced Tumor Cells," *Cancer Research*, 56:467-470.

Varki et al., (1984), "Antigens Associated with a human lung adenocarcinoma defined by monoclonal antibodies," *Cancer Research*, 44:681-687.

Verhoeyen et al., (1988), "Reshaping Human Antibodies: Grafting an Antilysozyme Activity," *Science*, 239:1534-1536.

Villunger et al., (1997), "Constitutive expression of Fas (Apo-1/CD95) ligand on multiple myeloma cells: a potential mechanism of tumor-induced suppression of immune surveillance," *Blood*, 90:1:12-20.

Watanabe et al., (1997), "Long-term depletion of naive T cells in patients treated for Hodgkin's disease," *Blood*, 90:9:3662-3672.

Wen et al., (1993). "Erythropoietin Structure-Function Relationships: High Degree of Sequence Homology Among Mammals," *Blood*, 82:1507-1516.

Williams et al., (1986), "Production of antibody-tagged enzymes by myeloma cells: application to DNA polymerase I Klenow fragment," *Gene*, 43:319-324.

Williams et al., (1987), "Diphtheria toxin receptor binding domain substitution with interleukin-2: genetic construction and properties of a diphtheria toxin-related interleukin-2 fusion protein," *Protein Engineering*, 1:6:493-498.

Wooley et al., (1993), "Influence of a Recombinant Human Soluble Tumor Necrosis Factor Receptor Fc Fusion Protein on Type II Collagen-Induced Arthritis in Mice," *Journal Immunology*, 151:6602-6607.

Wu et al., (1997), "Suppression of Tumor Growth with Recombinant Murine Angiostatin," *Biochemical and Biophysical Research Communications*, 236:651-654.

Xiang et al., (1997), "Elimination of Established Murine Colon Carcinoma Metastases by Antibody-Interleukin 2 Fusion Protein Therapy," *Cancer Research*, 57:4948-4955.

Zheng et al., (1995), "Administration of noncytolytic IL-10/Fc in muring models of lipopolysaccharide-induced septic shock and allogenic islet transplantation," *Journal of Immunology*, 154:5590-5600.

Xu et al., (1994), "Residue at Position 331 in the IgG1 and IgG4 CH2 Domains Contributes to Their Differential Ability to Bind and Activate Complement," *J. Biol. Chem.*, 269:3469-3474.

International Preliminary Examination Report for International Application Serial No. PCT/US02/38780, mailed Aug. 24, 2004 (3 pages).

International Search Report for International Application Serial No. PCT/US02/38780, mailed Jul. 21, 2003.

\* cited by examiner

US 7,186,804 B2

IL-2 FUSION PROTEINS WITH MODULATED SELECTIVITY

REFERENCE TO RELATED APPLICATIONS

This application claims priority to, and the benefit of U.S. Ser. No. 60/337,113, filed Dec. 4, 2001, and U.S. Ser. No. 60/371,966, filed Apr. 12, 2002, the entire disclosures of which are incorporated by reference herein.

FIELD OF THE INVENTION

The present invention relates generally to fusion proteins containing a cytokine, and methods to increase the therapeutic effectiveness of such fusion proteins. More specifically, the present invention relates to cytokine fusion proteins that exhibit a longer circulating half-life in a patient's body than the corresponding naturally occurring cytokine and that have improved therapeutic properties. In particular, the invention relates to IL2 fusion protein with improved therapeutic characteristics.

BACKGROUND

Interleukin-2 (IL-2) is a potent cytokine that acts on the immune system to generate primarily a cell-mediated immune response. Under the appropriate conditions, IL-2 is produced locally at high concentrations near the site of an antigen in order to supply the necessary co-stimulatory signals for generating an immune response to the antigen. Because of its role in the growth and differentiation of T cells, IL-2 has been a candidate in immunotherapeutic approaches to treating tumors. In addition to stimulating T cells, IL-2 has also been shown to stimulate B cells, NK cells, lymphokine activated killer cells (LAK), monocytes, macrophages and dendritic cells.

IL-2 is an approved therapeutic agent for the treatment of metastatic renal carcinoma and metastatic melanoma but its use is restricted due to severe toxic side effects, which include fever, nausea, vascular leakage and hypotension. Among the various toxic effects observed with IL-2 administration, the one toxic effect that is the least desirable and is believed to substantially interfere with IL-2 therapy is vascular leak syndrome (VLS) and the complications associated with it.

Therefore, there remains a need in the art to further enhance the therapeutic usefulness of IL-2 proteins.

SUMMARY OF THE INVENTION

The present invention is based, in part, upon the identification of mutations in the IL-2 moiety of an IL-2 fusion protein to increase the maximum tolerated dose of the protein relative to the dose of maximal effectiveness for that protein when administered to a patient. Preferred fusion proteins are able to bind by distinct interactions to more than one receptor species expressed on the same cell in the patient's body. Preferred cytokine fusion proteins include a cytokine that is able to bind to more than one type of cytokine receptor complex and to more than one cell type. The invention also provides methods to identify particular cytokine fusion protein variants with useful properties.

The present invention provides fusion proteins comprising a non-IL-2 moiety fused to a mutant IL-2 moiety, where the fusion protein exhibits a greater selectivity than a reference protein including the non-IL-2 moiety fused to a non-mutant IL-2 moiety, and where the selectivity is measured as a ratio of activation of cells expressing IL-2Rαβγ receptor relative to activation of cells expressing IL-2Rβγ receptor.

The mutant IL-2 moiety of the fusion proteins includes a mutation in one or more amino acids of the mature human IL-2 protein. In one embodiment, fusion proteins according to the invention include an amino acid substitution at one or more amino acid positions in the IL-2 moiety. In another embodiment, fusion proteins of the invention include deletions of amino acids at one or more amino acid positions in the IL-2 moiety. In yet another embodiment, fusion proteins of the invention include modifications of one or more amino acids in the IL-2 moiety of the fusion proteins.

Mutations in the fusion proteins of the invention alter the selectivity of fusion proteins relative to a reference fusion protein, where the selectivity is measured as a ratio of activation of cells expressing IL-2Rαβγ receptor relative to activation of cells expressing IL-2Rβγ receptor. Mutations in the fusion proteins can also result in a differential effect on the fusion protein's affinity for IL-2Rβγ receptor relative to the fusion protein's affinity for IL-2Rαβγ receptor. Preferred mutations or alterations reduce a fusion protein's activation of cells expressing IL-2Rβγ receptor relative to the fusion protein's activation of cells expressing IL-2Rαβγ receptor.

Preferred fusion proteins of the invention generally exhibit a differential effect that is greater than about 2-fold. In one aspect, the differential effect is measured by the proliferative response of cells or cell lines that depend on IL-2 for growth. This response to the fusion protein is expressed as an ED50 value, which is obtained from plotting a dose response curve and determining the protein concentration that results in a half-maximal response. The ratio of the ED50 values obtained for cells expressing IL-2Rβγ receptor to cells expressing IL-2Rαβγ receptor for a fusion protein of the invention relative to the ratio of ED50 values for a reference fusion protein gives a measure of the differential effect for the fusion protein.

The selectivity of fusion proteins of the invention may be measured against a reference fusion protein comprising the same non-IL-2 moiety as in the fusion protein fused to a non-mutant IL-2 moiety. In a preferred embodiment, a differential effect measured for the fusion proteins of the invention, as described above, is between about 5-fold and about 10-fold. Preferably, the differential effect exhibited by the fusion proteins of the invention is between about 10-fold and about 1000-fold.

In an alternative preferred embodiment, the selectivity of the fusion protein is compared to the selectivity of a reference fusion protein that comprises the same non-IL-2 moiety as in the fusion protein fused to an IL-2 moiety including mature human IL-2 with an amino acid substitution at position 88 changing an asparagine to an arginine (N88R). Fusion proteins of the invention that have an improved therapeutic index include fusion proteins having a selectivity close to that of N88R but between about 0.1% to about 100% of the selectivity of a reference fusion protein with the N88R amino acid substitution. In another embodiment, fusion proteins of the invention have a selectivity between about 0.1% to about 30% of the selectivity of a reference fusion protein with the N88R amino acid substitution in the IL-2 moiety. Fusion proteins of the invention also include fusion proteins that have a selectivity between about 1% to about 20% of the selectivity of the reference fusion protein with the N88R amino acid substitution in the IL-2 moiety. Selectivity of fusion proteins of the invention can also be between about 2% to about 10% of the selectivity of the reference fusion protein including the N88R amino acid substitution in the mature human IL-2 moiety.

Fusion proteins of the invention have a serum half-life that is longer than the serum half life of mature human IL-2 protein. The long serum half-life of fusion proteins of the invention can be attributed to the non-IL-2 moiety of the fusion protein. For example, in one embodiment, the non-IL-2 moiety of a fusion protein of the invention is albumin. In another embodiment, the non-IL2 moiety of a fusion protein of the invention is an antibody domain including, for example, variants of the KS-1/4 antibody domain, variants of the NHS76 antibody domain and variants of the 14.18 antibody domain. The antibody domain can also be selected from a variety of other antibodies, for example, antibodies against various tumor and viral antigens.

In a preferred embodiment, a differential effect measured for the fusion proteins of the invention, as described above, is between about 5-fold and about 10-fold. Preferably, the differential effect exhibited by the fusion proteins of the invention is between about 10-fold and about 1000-fold.

It is useful to mutate amino acids in the IL-2 moiety of fusion proteins of the invention that result in a differential effect which is 2-fold or greater. Different amino acid mutations in the IL-2 moiety result in a differential effect greater than about 2-fold, between about 5-fold and about 10-fold, or preferably between about 10-fold and about 1000-fold. In a preferred embodiment, the amino acid mutation is a substitution of the aspartic acid corresponding to position 20 of the mature human IL-2 moiety with a threonine (D20T). In yet another preferred embodiment, the amino acid mutation is a substitution of the asparagine at position 88 of the mature human IL-2 protein with an arginine (N88R). Fusion proteins of the invention can also include mutations at more than one amino acid positions. In one embodiment, a fusion protein according to the invention includes amino acid substitutions changing an asparagine to an arginine at position 88, a leucine to a threonine at position 85 and an isoleucine to a threonine at position 86 of the mature human IL-2 protein.

Mutations of amino acids at certain positions in the IL-2 moiety results in a differential effect that is greater than about 2-fold. It is useful to mutate amino acids corresponding to positions K8, Q13, E15, H16, L19, D20, Q22, M23, N26, H79, L80, R81, D84, N88, I92, and E95 of the mature human IL-2 protein. Additional useful amino acid positions that can be mutated are L25, N31, L40, M46, K48, K49, D109, E110, A112, T113, V115, E116, N119, R120, I122, T123, Q126, S127, S130, and T131 of the mature human IL-2 protein. Preferred amino acid positions that are mutated in fusion proteins of the invention include D20, N88, and Q126.

In one embodiment, one or more amino acid at the preferred positions listed above are mutated in the fusion proteins. In a preferred embodiment, the amino acid asparagine at position 88 is substituted with an arginine (N88R). In another preferred embodiment, the amino acid aspartic acid at position 20 is substituted with a threonine (D20T). In yet another preferred embodiment, the glutamine at position 126 is substituted with an aspartic acid (Q126D). The various amino acid substitutions result in a selectivity in the activity of fusion proteins of the invention for IL-2Rαβγ receptor bearing cells relative to IL-2Rβγ receptor bearing cells, which can be reflected in the fusion protein's affinity for an IL-2Rβγ receptor relative to the fusion protein's affinity for an IL-2Rαβγ receptor.

Fusion proteins with mutations at one or more amino acid positions described above have a differential effect that is greater than about 2-fold. Preferably, the differential effect is between about 5-fold and about 10-fold and more preferably between about 10-fold and about 1000-fold.

In addition to mutating amino acids in the IL-2 moiety, amino acids in the non-IL-2 moiety can also be mutated. In a preferred embodiment, the non-IL-2 moiety is an antibody domain. The antibody domain can be selected from a variety of different immunoglobulin (Ig) antibodies, preferably IgG antibodies, including for example, IgG gamma 1, IgG gamma 2 and IgG gamma 4 antibody domains, or any combination of these antibody domains. As used herein, the terms "antibody" and "immunoglobulin" are understood to mean (i) an intact antibody (for example, a monoclonal antibody or polyclonal antibody), (ii) antigen binding portions thereof, including, for example, an Fab fragment, an Fab' fragment, an (Fab')$_2$ fragment, an Fv fragment, a single chain antibody binding site, an sFv, (iii) bi-specific antibodies and antigen binding portions thereof, and (iv) multi-specific antibodies and antigen binding portions thereof. In proteins of the invention, an immunoglobulin Fc region can include at least one immunoglobulin constant heavy region, for example, an immunoglobulin constant heavy 2 (CH2) domain, an immunoglobulin constant heavy 3 (CH3) domain, and depending on the type of immunoglobulin used to generate the Fc region, optionally an immunoglobulin constant heavy 4 (CH4) domain, or a combination of the above. In particular embodiments, the immunoglobulin Fc region may lack an immunoglobulin constant heavy 1 (CH1) domain. Although the immunoglobulin Fc regions may be based on any immunoglobulin class, for example, IgA, IgD, IgE, IgG, and IgM, immunoglobulin Fc regions based on IgG are preferred. An antibody moiety included in a fusion protein of the invention is preferably human, but may be derived from a murine antibody, or any other mammalian or non-mammalian immunoglobulin. It is contemplated that an Fc region used in a fusion protein of the invention may be adapted to the specific application of the molecule. In one embodiment, the Fc region is derived from an immunoglobulin γ1 isotype or a variant thereof. In another embodiment, the Fc region is derived from an immunoglobulin γ2 isotype or a variant thereof. In further embodiments, the Fc region may be derived from an immunoglobulin γ3 isotype or a variant thereof. The Fc region may comprise a hinge region that is derived from a different immunoglobulin isotype than the Fc region itself. For example, the Fc region may be derived from an immunoglobulin γ2 isotype and include a hinge region derived from an immunoglobulin γ1 isotype or a variant thereof. In yet another preferred embodiment of the invention, the Fc region is derived from an immunoglobulin γ4 isotype. Immunoglobulin γ4 isotypes that have been modified to contain a hinge region derived from an immunoglobulin γ1 isotype or a variant thereof are particularly preferred.

In one embodiment, fusion proteins of the invention comprise mutations in the Ig moiety. A useful mutation is a mutation in the IgG gamma 1 sequence QYNSTYR (SEQ ID NO: 1), changing the N to a Q; a particularly useful mutation is a mutation in the gamma 2 or 4 sequence QFNST (SEQ ID NO: 2), changing the dipeptide motif FN to AQ.

The invention also features DNA constructs encoding various fusion proteins of the invention. The fusion proteins of the invention are particularly useful for treating cancer, viral infections and immune disorders.

These and other objects, along with advantages and features of the invention disclosed herein, will be made more apparent from the description, drawings, and claims that follow.

BRIEF DESCRIPTION OF THE DRAWINGS

FIG. 1 illustrates the fusion of a cytokine to a second protein moiety that alters the natural binding characteristics of the cytokine.

DETAILED DESCRIPTION OF THE INVENTION

Figure 1A:
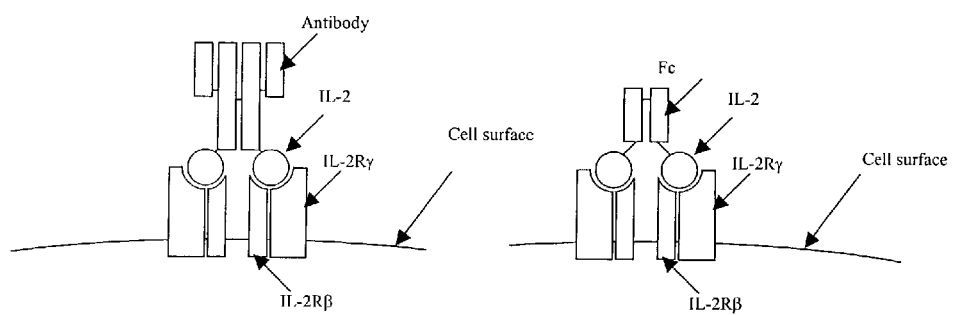
FIG. 1A depicts the fusion partner to IL-2 as a dimeric molecule, such as an antibody or the Fc portion of an Fc-containing fusion protein, and therefore two molecules of IL-2 are brought to the cell surface when the IL-2 moiety of the fusion protein interacts with its receptor.

The invention provides methods and compositions that enhance the therapeutic index of IL-2 fusion proteins and IL-2 immunocytokines in particular. According to the invention, the therapeutic index of a therapeutic molecule is a measure of the ratio of the maximum tolerated dose of a molecule divided by the dose of maximal effectiveness for that molecule. The invention includes improved variants of IL-2 immunocytokines that exhibit a significantly longer circulating half-life compared to free IL-2. The invention also provides IL-2 fusion proteins, and in particular IL-2 immunocytokines, that exhibit a selective IL-2 response, reflected by reduced activation of cells with various effector functions by the fusion proteins of the invention, which is a leading cause of the toxic effects of IL-2. In addition, the invention provides IL-2 fusion proteins with improved activity. An IL-2 fusion protein of the invention includes changes at one or more amino acid positions that alter the relative affinity of the IL-2 fusion protein for different IL-2 receptors, resulting in altered biological properties of the IL-2 fusion protein. The invention is useful to reduce or minimize any toxicity associated with IL-2 therapy. Regardless of the underlying mechanism of any given IL-2 toxicity, such as VLS, the toxicity results in part from the fact that IL-2 is administered intravenously and therefore acts systemically within the body, even though the effect of IL-2 is desired at a specific site. This problem is exacerbated by the fact that a systemic administration of IL-2 requires a much higher dose than a localized administration would, which in turn may promote toxicities that would not be seen at lower doses. The invention provides IL-2 fusion proteins with reduced toxicity. The invention also provides methods for making IL-2 fusion proteins with reduced toxicity.

In general, the invention is useful for fusion proteins including an IL-2 moiety fused to a non-IL-2 moiety. According to the invention, a non-IL-2 moiety can be a synthetic or a natural protein or a portion or variant (including species, allelic and mutant variants) thereof. Preferred non-IL-2 moieties include Fc and albumin moieties. According to the invention, an IL-2 moiety can be a natural IL-2 molecule or a portion or variant (including species, allelic and mutant variants) thereof that retains at least one IL-2 activity or function (an IL-2 moiety can be an IL-2 that is modified to have a different IL-2 receptor binding affinity according to the invention).

According to the invention, cells respond to IL-2 through specific cell surface receptors (IL-2R), which exist in two forms. The high affinity receptor is heterotrimeric, consisting of $\alpha$, $\beta$ and $\gamma$ subunits; the intermediate affinity receptor is heterodimeric, consisting of $\beta$ and $\gamma$ subunits. Binding constants of IL-2 for these two forms of IL-2R differ by two orders of magnitude. Signal transduction is mediated on the cytoplasmic side of the receptor through interactions within the $\beta\gamma$ complex. Different cell types express the $\alpha$, $\beta$ and $\gamma$ subunits in varying amounts. For instance, activated T cells express all of the subunits to form the high affinity IL-2R$\alpha\beta\gamma$, whereas mature resting T cells and NK cells express the $\beta$ and $\gamma$ subunits to give the intermediate affinity IL-2R$\beta\gamma$. Thus, cells require different levels of exposure to IL-2 for stimulation, and conversely, by regulating IL-2 activity within a specific cellular context, the nature of an immune response can be controlled.

Methods and compositions of the invention are particularly useful in the context of IL-2 fusion proteins such as IL-2 bearing immunocytokines. According to the invention, IL-2 bearing immunocytokines are synthetic molecules that have been shown to significantly increase the efficacy of IL-2 therapy by directly targeting IL-2 into a tumor microenvironment. Immunocytokines are fusion proteins consisting of an antibody moiety and a cytokine moiety, such as an IL-2 moiety. According to the invention, an antibody moiety can be a whole antibody or immunoglobulin or a portion or variant (including species, allelic and mutant variants) thereof that has a biological function such as antigen specific binding affinity. Similarly, a cytokine moiety of the invention can be a natural cytokine or a portion or variant (including species, allelic and mutant variants) thereof that retains at least some cytokine activity. The benefits of an immunocytokine therapy are readily apparent. For example, an antibody moiety of an immunocytokine recognizes a tumor-specific epitope and results in targeting the immunocytokine molecule to the tumor site. Therefore, high concentrations of IL-2 can be delivered into the tumor microenvironment, thereby resulting in activation and proliferation of a variety of immune effector cells mentioned above, using a much lower dose of the immunocytokine than would be required for free IL-2. In addition, the increased circulating half-life of an immunocytokine compared to free IL-2 contributes to the efficacy of the immunocytokine. And finally, the natural effector functions of an antibody also may be exploited, for instance by activating antibody dependent cellular cytotoxicity (ADCC) in Fc$\gamma$RIII bearing NK cells.

An IL-2 immunocytokine has a greater efficacy relative to free IL-2. However, some characteristics of IL-2 immunocytokines may aggravate potential side effects of the IL-2 molecule. Because of the significantly longer circulating half-life of IL-2 immunocytokines in the bloodstream relative to free IL-2, the probability for IL-2 or other portions of the fusion protein molecule to activate components generally present in the vasculature is increased. The same concern applies to other fusion proteins that contain IL-2 fused to another moiety such as Fc or albumin, resulting in an extended half-life of IL-2 in circulation.

The invention provides altered IL-2 fusion proteins, such as IL-2 fused to an intact antibody or to a portion of an antibody, or to albumin, with reduced toxicity compared to unaltered forms of such fusion proteins. The invention also provides fusion proteins with one or more alterations in the IL-2 and/or the non-IL-2 moieties that alter the relative activity of the fusion protein in cells expressing the $\alpha$, $\beta$, and $\gamma$ IL-2 receptor subunits compared to cells expressing the $\beta$ and $\gamma$ IL-2 receptor subunits. The invention also provides for altered IL-2 containing fusion proteins that exhibit an altered affinity towards the α, β, or γ subunit of the IL-2 receptor compared to unaltered forms of such fusion proteins.

A number of IL-2-containing antibody fusion proteins exhibit IL-2 activity that is quantitatively altered with respect to free IL-2, but is not qualitatively optimal for therapeutic applications. The invention provides modified forms of antibody-IL2 fusion proteins in which IL-2 or the antibody, or both moieties, are altered to qualitatively improve the IL-2 activity for a given application.

The invention also provides strategies for determining the types of modifications that are particularly useful in designing modified fusion proteins for treatment of diseases.

Figure 1B:
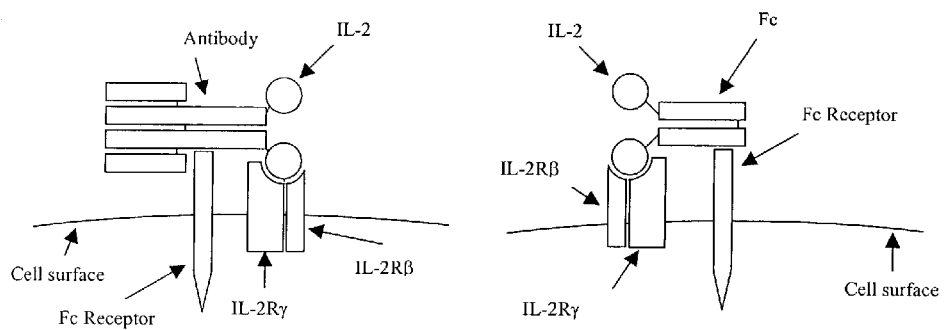
FIG. 1B illustrates a second mechanism that produces the same effect.

FIG. 1 illustrates possible mechanisms by which a fusion protein may bind to a cell surface, such that the receptor-binding properties of a moiety within the fusion protein are altered. For example, FIG. 1A depicts the fusion partner to IL-2 as a dimeric molecule. This increases the probability that the second IL-2 molecule interacts with its receptor, for example by decreasing the off-rate, which leads to a net increase in binding. FIG. 1B illustrates a second mechanism that produces the same effect. In cells that bear both a receptor for IL-2 and a receptor for the IL-2 fusion partner of the fusion protein (e.g. an Fc receptor for the Fc part of an Ig moiety) the receptor for the fusion partner (e.g. the Fc receptor) can engage the fusion protein and tether it at the cell surface where it now has an increased likelihood to bind to an IL-2 receptor.

A Phase I/II trial of an antibody-cytokine fusion protein, termed huKS-IL2, was recently completed. huKS-IL2 is a fusion protein consisting of the KS-1/4 antibody fused to the cytokine, interleukin-2. KS-1/4 recognizes the tumor cell surface antigen EpCAM (epithelial cell adhesion molecule) and has the effect of concentrating IL-2 at the tumor site. In the course of this trial, patient responses to treatment were measured. One patient who showed significant response to the therapy experienced a clinical partial response followed by disease stabilization and reduction in the use of pain medication. The patient had already received prior standard treatments that had failed. The patient's life was extended significantly beyond what was expected in the absence of such treatment.

Surprisingly, as a result of prior chemotherapy, this patient's T cell population was essentially obliterated. This patient had much lower T cell counts than all the other patients in the trial. Given that IL-2 is known to activate T cells and, for example, is known to enhance the cytotoxicity of CD8(+) T cells toward tumor cells, the strong response of this patient apparently lacking T cells was particularly unexpected. This observation prompted further study of novel antibody-IL-2 fusion proteins in which the IL-2 moiety might exhibit altered cell specificity, resulting in an improvement in the therapeutic index of IL-2 fusion proteins.

From the crystal structure of IL-2, sequence comparisons with related cytokines, and site-directed mutagenesis studies, much progress has been made in elucidating amino acids in IL-2 that come in contact with different IL-2 receptor subunits and their consequence on biological activity. For instance, the D20 residue, conserved in IL-2 across mammalian species, is a critical residue for binding the β subunit of the IL-2 receptor and various substitutions at this position have distinct effects. For example, the variant IL-2(D20K) fails to bind to any IL-2R complex and is generally inactive, while variants IL-2(D20E) or IL-2(D20T) retain their biological activity. Amino acid positions R38 and F42 are critical for binding the α subunit, and while mutations at these sites diminish the interaction of IL-2 with the high affinity receptor IL-2Rαβγ, it still binds to the intermediate affinity receptor IL-2Rβγ and thus some bioactivity is retained. N88 is another residue that is involved in mediating interactions with the β subunit, and while the IL-2 (N88R) variant has greatly reduced affinity for the intermediate affinity receptor, its affinity for the high affinity receptor is essentially unchanged. The N88R mutant of IL-2 is therefore still able to activate T cells.

Binding affinity of fusion proteins of the invention for different receptors can be determined by a number of methods known in the art including, for example, a radioimmunoassay.

It is thus possible to perturb the IL-2 structure so that it displays greater affinity toward one IL-2 receptor complex compared with another IL-2 receptor complex by mutating a specific amino acid that contacts one of the receptor subunits, or by altering a combination of amino acid residues. As a consequence, the molecule displays greater activity in one cell type versus another. According to the invention, it is possible to manipulate the structure of IL-2 in the context of an Ig-IL2 fusion protein to obtain the desired effect. Moreover, in some instances, the Ig-IL2 variant fusion protein possesses different biological characteristics compared to the corresponding free IL-2 mutant protein.

It is furthermore possible, according to the invention, to manipulate the IL-2 moiety in a fusion protein so that it displays an altered affinity toward one or more of the IL-2 receptor subunits (α, β, or γ) and results in an overall decrease in bioactivity of the fusion protein. Such variants are able to activate IL-2 responsive cells, but require a higher concentration than free IL-2. Accordingly, when IL-2 fusion proteins are concentrated at a desired target site, for example by a targeting moiety, these variants have an improved therapeutic index.

The α receptor subunit of IL-2R appears to play a tethering function: this low-affinity receptor binds to IL-2 and keeps IL-2 close to the cell surface, so that the effective concentration in the neighborhood of cell surface IL-2Rβ and IL-2Rγ receptor subunits is increased. Together, the α-subunit and the βγ-subunits of the IL-2 receptor create the high affinity IL-2R complex. The invention is based, in part, on the recognition that IL-2 fusion proteins can engage in multiple and distinct interactions with receptors on the cell surface. For example, in the case of fusion proteins containing an antibody moiety, the antibody moiety itself may promote binding of the fusion protein to the cell surface and furthermore, IL-2 may be present in multiple copies in the fusion protein. As a result, IL-2 may be tethered to a cell expressing only the β and γ subunits of IL-2R, and have an enhanced ability to activate such a cell.

For example, a dimeric immunoglobulin (Ig) fused to IL-2 possesses two copies of IL-2, such that the binding of one IL-2 moiety to its receptor enhances the probability of an interaction of the second IL-2 moiety with a receptor molecule on the same cell surface. The diagram in FIG. 1A represents a possible configuration of an Ig-IL2 fusion protein on a cell surface. The invention provides Ig-IL2 fusion proteins in which the IL-2 moiety is altered to reduce binding to an IL-2Rβγ receptor.

A second mechanism by which Ig-IL2 fusion proteins may have altered binding to the surface of certain immune cells is that the Fc receptor on a cell surface may bind to the Fc part of an Ig moiety and thus tether the IL-2 to the surface of cells possessing both an Fc receptor and an IL-2 receptor (FIG. 1B). Such cells include NK cells, B cells, and macrophages. The invention provides Ig-IL2 fusion proteins in which the Ig moiety is altered to reduce binding to an Fc receptor. The invention further provides Ig-IL2 fusion proteins in which both the Ig-moiety and the IL-2 moiety incorporate alterations of the nature described above.

Based on the insight that Ig-IL2 fusion proteins may be artificially tethered to cells bearing IL-2 receptor subunits, it is possible to design variant fusion proteins in which the tethering moiety is altered. For example, it is useful to alter the Fc-receptor binding features of an Ig-IL2 fusion protein. This may be done, for example, by mutating known amino acid contact sites within the Fc moiety or by removing the N-linked glycosylation sites, either by mutation or by enzymatic digestion of the protein.

Similarly, according to the invention it is useful to introduce mutations within the IL-2 moiety that have an effect on binding to IL-2 receptor subunits. In particular, it is useful to mutate amino acids in IL-2 that come into contact with the β subunit of IL-2 receptor. A particularly useful type of mutation is one that reduces the energy of binding between IL-2 and IL-2Rβ, but does not sterically hinder this interaction. For example, mutation of a contact amino acid to an amino acid with a smaller side chain is particularly useful. The effect of such mutations is to reduce affinity of IL-2 for the β-γ form of IL-2 receptor by a significant degree and also to reduce the activation of the signaling pathway mediated by these receptors, but to have relatively little or no effect on binding to the α-β-γ form of the IL-2 receptor or on the activity elicited by IL-2 in cells bearing such IL-2 receptors. In a preferred embodiment of the invention, a mutation reduces the affinity for the β-γ form of the IL-2 receptor, but does not eliminate it.

Similarly, it is useful to introduce mutations in amino acids on the surface of IL-2 that interact with the α subunit of IL-2 receptor. A particularly useful type of mutation is one that reduces the energy of binding between IL-2 and IL-2Rα, but does not sterically hinder this interaction. For example, mutation of a contact amino acid to an amino acid with a smaller side chain is particularly useful. The effect of such mutations is to reduce the affinity for the α-β-γ form of IL-2 receptor to a significant extent, but to have relatively little or no effect on binding to the β-γ form of the IL-2 receptor. In a preferred embodiment of the invention, a mutation reduces the affinity for the α-β-γ form of the IL-2 receptor, but does not eliminate it.

Similarly, it is also useful to introduce mutations in amino acids on the surface of IL-2 that interact with the γ subunit of IL-2 receptor. As in the preceding cases, a particularly useful type of mutation reduces the energy of binding between IL-2 and IL-2Rγ, but does not sterically hinder this interaction. For example, mutation of a contact amino acid to an amino acid with a smaller side chain is particularly useful. The effect of such mutations is to reduce the affinity for the β-γ form of IL-2 receptor to a significant extent, but to have relatively little or no effect on binding to the α-β-γ form of the IL-2 receptor. In a preferred embodiment of the invention, a mutation reduces the affinity for the β-γ form of the IL-2 receptor, but does not eliminate it.

It is also useful to introduce a combination of amino acid mutations into IL-2 that interact with different surfaces of the IL-2 receptor subunits. While each mutation independently may have little or no effect on binding of IL-2 to either the α-β-γ or the β-γ form of the IL-2 receptor, the combination of mutations may achieve the desired reduction in affinity of IL-2 for its receptor or the bioactivity of IL-2.

According to the invention, mutations in other parts of IL-2 indirectly contribute to alterations in the interaction of IL-2 with either the β-γ form or the α-β-γ form of the IL-2 receptor, and thereby result in an IL-2 molecule with modulated activity. For instance, a mutation may slightly alter the conformation of the molecule and alter its binding properties.

According to the invention, it is also useful to produce fusion proteins that contain mutations in the IL-2 moiety that modulate binding of the IL-2 moiety to an IL-2 receptor complex and also mutations in the antibody moiety. These fusion proteins may be particularly useful if it is desired to alter the interaction of the Ig-IL2 fusion protein with particular Fc receptors.

A free IL-2 moiety can display different binding characteristics for an IL-2R complex than when the IL-2 moiety is fused to another protein moiety such as an Ig. One possible mechanism by which this occurs is presented above. Another possible mechanism is that IL-2 is sterically or conformationally constrained in the context of the immunocytokine and that the particular constraint is reflected in the binding characteristics of the IL-2 moiety towards the different IL-2 receptor complexes. It is therefore useful to introduce alterations in the fusion protein that will modulate this constraint. For example, changes in the non-IL-2 moiety are useful in modulating the activity of IL-2.

The usefulness of a particular IL-2 fusion protein, such as an Ig-IL2 fusion or an IL-2 fusion protein containing Fc or albumin, for a particular application, such as treatment of human disease, is tested in an appropriate cellular or animal model. When possible, testing in an animal is preferred, because such testing comes closer to the full complexity of the behavior of the immune system in a human disease. For example, a particular balance of certain cells may be optimal to fight a disease of interest, such as cancer or an infection with a bacterium, virus, or parasite. For example, a relatively high level of T cell activity may be useful against a certain tumor type, while a relatively high level of NK cell activity may be useful against a different tumor type.

Another feature of the invention is IL-2 fusion protein variants, such as Ig-IL2 fusions or IL-2 fusions containing Fc or albumin, with superior toxicity profiles. For example, an Ig-IL2 fusion protein containing the mutation D20T shows reduced toxicity in animals such as mice as compared to corresponding Ig-IL2 fusion proteins with D at position 20. In another example, an Ig-IL2 fusion protein containing the mutation N88R or the combination of mutations L85T, I86T, N88R in the IL-2 moiety shows reduced toxicity in animals such as mice as compared to corresponding Ig-IL2 fusion proteins with N at position 88. In addition, an antibody-IL2 fusion protein containing the mutation D20T or the mutation N88R in the IL-2 moiety shows comparable potency to the corresponding parental antibody-IL2 fusion protein when used to treat a tumor that expresses an antigen target of the antibody.

The properties of the D20T variant of Ig-IL2 fusion proteins is particularly surprising in light of the reported properties of the D20T mutation in the free IL-2 protein. Specifically, the D20T mutation in the free IL-2 protein does not display a difference relative to the wild-type IL-2 protein in its activity towards IL-2Rαβγ-bearing cells or IL2R-βγ-bearing cells (Shanafelt et al., PCT WO99/60128). However, an Ig-IL2 fusion protein containing the D20T mutation has a drastically reduced potency in activation of IL2R-βγ-bearing cells, but has essentially normal potency in activating IL-2Rαβγ-bearing cells.

Accordingly, mutation of several amino acids within the IL-2 moiety of an Ig-IL2 fusion protein leads to reduced toxicity while having relatively little effect on the potency of the fusion protein in the treatment of various diseases. For instance, the extent to which the affinity of an IL-2 fusion protein variant for its receptors may be altered is a function of how well the particular fusion protein is concentrated at its intended target site. It is particularly useful to mutate one or more of the following amino acids within the IL-2 moiety: Lys8, Gln13, Glu15, His16, Leu19, Asp20, Gln22, Met23, Asn26, Arg38, Phe42, Lys43, Thr51, His79, Leu80, Arg81, Asp84, Asn 88, Val91, Ile92, and Glu95. It is also useful to mutate one or more of the following amino acids within the IL-2 moiety: Leu25, Asn31, Leu40, Met46, Lys48, Lys49, Asp109, Glu110, Ala112, Thr113, Val115, Glu116, Asn119, Arg120, Ile122, Thr123, Gln126, Ser127, Ser130, and Thr131.

This invention discloses forms of an Ig moiety fused to IL-2, for example antibody-IL2 fusions such as huKS-IL2 or dI-NHS76-IL2, in which changes in the Ig moiety fused to IL-2 affect the binding properties of the fusion protein to the IL-2R complex. These changes may be amino acid substitutions in the amino acid sequence of the heavy chain, or chemical modifications. Useful amino acid substitutions include those that affect the glycosylation of the fusion protein or that directly affect interaction with an Fc receptor. A particularly useful substitution may be one that inhibits the glycosylation normally found at position N297 (EU nomenclature) of the IgG heavy chain. Chemical and biochemical modifications include PEGylation of the molecule or treatment with N-glycanase to remove N-linked glycosyl chains. Without wishing to be bound by theory, one may envisage that specific changes in the antibody portion of the molecule could affect the conformation of IL-2, for instance by altering the rigidity of the antibody molecule. In the case of huKS-IL2, these alterations may lead to a KS-IL2 molecule which now shows an increased selectivity towards T cells in a cell based bioassay.

For antibody-IL2 fusion proteins it is often useful to select an Ig moiety that confers other desired properties to the molecule. For example, an IgG moiety of the gamma 1 subclass may be preferred to maintain immunological effector functions such as ADCC. Alternatively, an IgG moiety of the gamma 2 or gamma 4 subclasses may be preferred, for example to reduce FcR receptor interactions. When using IgG moieties of subclasses gamma 2 or gamma 4, inclusion of a hinge region derived from gamma 1 is particularly preferred.

It is often useful to use the mutations and chemical or biochemical modifications of Ig-IL2 fusion proteins in combination with other mutations having distinct useful properties, such as the mutation of the lysine at the C-terminus of certain Fc regions to an alanine or another hydrophobic residue. For example, it is particularly useful to apply the modifications of the invention to the antibody fusion protein huKS-ala-IL2 or dI-NHS(76)-ala-IL2. It is also preferred to introduce further mutations into the molecule that eliminate potential T-cell epitopes. It is particularly preferred that these mutations do not substantially alter the desired properties of the molecule.

This invention further discloses forms of an Ig moiety fused to IL-2, for example an antibody-IL2 fusion such as huKS-IL2, in which a specific alteration in the amino acid sequence of IL-2, for example IL2(D20T) or IL2(N88R) changes the binding properties of the fusion protein to the IL-2R complex. The amino acid sequence of mature human IL-2 protein is depicted in SEQ ID NO: 3. The changes in binding properties are reflected in an increased selectivity towards T cells in a cell based bioassay. The particular mutation influences the degree of selectivity towards T cells.

In addition, these changes result in a fusion molecule, for instance huKS-ala-IL2(D20T) or huKS-ala-IL2(N88R), with less toxic side effects when administered to mice systemically than, for instance huKS-ala-IL2. Also, these changes lead to a fusion protein, for instance huKS-ala-IL2 (N88R), that is at least as efficacious as the normal huKS-IL2 or huKS-ala-IL2 in tumor therapy in a number of mouse tumor models.

Because the immunological responses required to clear a tumor are manifold and also vary from tumor type to tumor type, it may not be desirable to completely eliminate a functionality from the molecule when a molecule with reduced toxicity is used. For instance, in a mouse model where pulmonary metastasis of colon carcinoma was induced, huKS-IL2 was shown to effectively treat the cancer by a T cell mediated mechanism, which did not require NK cells, whereas in a mouse model for neuroblastoma, the elimination of the tumor by huKS-IL2 was shown to require NK cells but not T cells. Therefore, there are cases where the selectivity profile may be more appropriately modulated to still allow an NK mediated response. In one embodiment of the invention, a more desirable approach is to subtly alter the selectivity profile of the molecule such that a response involving multiple receptor types is still achieved, most preferably at the sites where the molecule is concentrated. For example, the invention provides alterations of an Ig-IL2 fusion protein in which the selectivity for the IL-2Rαβγ, relative to IL-2Rβγ, is enhanced 2- to 10-fold, 10- to 100-fold, 100- to 1000-fold, or more than 1000-fold, relative to a corresponding unmodified Ig-IL2 fusion protein.

Another object of the invention is to provide for optimal uses of Ig-IL2 fusion proteins with reduced toxicity for the treatment of cancer or infectious disease. While altered selectivity may lead to reduced vascular toxicity, it may not lead to optimal increases in the therapeutic index upon increasing the dose of the fusion protein. For example, these increases in dose may lead to an induction of negative regulatory mechanisms that regulate immune responses. It may therefore be useful to use treatment modalities that combine low-toxicity Ig-IL2 fusion proteins with agents that decrease such effects.

One recently identified potent inhibitor of cellular immune responses is a class of $CD4^+CD25^+$ regulatory T cells that express the high affinity IL-2R (for a review, see Maloy and Powrie, (2001) Nature Immunol. 2:816). According to the invention, increased doses of low-toxicity Ig-IL2 fusion proteins may additionally activate these cells. Upon stimulation, these cells up-regulate CTLA-4 on their cell surface, which engage cell surface molecules B7-1 and B7-2 on immune cells and in turn elicit a potent negative signal (Takahashi et al., (2000) J. Exp. Med. 192: 303). Thus, inhibitors of these processes could be useful in combination therapy with fusion proteins of the invention. In one embodiment, antibodies neutralizing CTLA-4 and its effects can be used. In another embodiment, other proteins with similar activity can be used, such as soluble B7 receptors and their fusion proteins (e.g. B7-Ig). Further embodiments include the use of antibodies that kill or inhibit these regulatory T cells themselves such as anti-CD4 and anti-CD25. In a preferred embodiment, the latter are administered sequentially rather than simultaneously.

According to the invention, another useful mechanism involves overstimulation of cyclo-oxygenase 2 (COX-2) leading to the production of prostaglandins, which are known to inhibit immune responses (see PCT US99/08376). Therefore, a further embodiment combines the use of the low-toxicity Ig-IL2 molecules with COX-2 inhibitors such as Indomethacin, or the more specific inhibitors Celecoxib (Pfizer) and Rofecoxib (Merck&Co). It is understood that still other immune mechanisms might be activated by increasing doses of low-toxicity Ig-IL2 fusion proteins and that combination therapies may be devised to address these mechanisms. In addition, low doses of certain cytotoxic drugs, such as cyclophosphamide, which have immune potentiating effects in vivo may be useful therapeutic agents to include in a combination therapy.

Fusions of albumin have been developed with the purpose of generating therapeutic fusion proteins with enhanced serum half-lives. For example, Yeh et al. (Yeh P, et al. Proc Natl Acad Sci USA. [1992] 89:1904–8.) constructed an albumin-CD4 fusion protein that had a much longer serum half-life than the corresponding CD4 moiety alone.

It is useful to construct fusions of albumin to IL-2, erythropoietin, interferon-alpha, and other ligands. These fusion proteins have longer serum half-lives than the corresponding ligand alone. Such fusions may be constructed, in the N- to C-terminal direction, as ligand-albumin fusions or albumin-ligand fusions, using standard genetic engineering and protein expression techniques. Alternatively, albumin and a ligand may be joined by chemical conjugation.

However, albumin-ligand fusion proteins often have undesirable properties. Without wishing to be bound by theory, one reason for why albumin-ligand fusion proteins may have undesirable properties is the fact that there are receptors for albumin on vascular endothelial cells (Tiruppathi et al. Proc Natl Acad Sci USA. [1996] 93:250–4). As a result, the effects of a ligand on vascular endothelial cells may be enhanced.

For example, an albumin-IL2 fusion protein has an enhanced serum half-life, but also causes enhanced vascular leak. Without wishing to be bound by theory, it is noted that activation of IL-2 mediated responses in the vasculature is increased because of binding of the fusion protein to albumin receptors present on endothelial cells of the vasculature. Binding of albumin-IL2 fusion proteins to cells that have receptors both for albumin and IL-2 is enhanced by a mechanism analogous to that shown in FIG. 1b for the enhancement of binding of an Ig-ligand fusion protein to a cell surface.

To reduce the vascular leak caused by albumin-IL2, it is useful to introduce mutations into the IL-2 moiety that specifically reduce IL-2's affinity for IL-2Rβγ receptors. For example, an albumin-IL2(N88R) or albumin-IL2(D20T) fusion protein is constructed and subsequently found to have reduced toxicity and an enhanced therapeutic index for a disease model in an animal such as a mouse.

Molecules of the present invention are useful for the treatment of malignancies and tumors, particularly treatment of solid tumors. Examples of tumors that can be treated according to the invention are tumors of epithelial origin such as those present in, but not limited to, ovarian cancer, prostate cancer, stomach cancer, hepatic cancer, bladder, head and neck cancer. Equally, according to the invention, malignancies and tumors of neuroectodermal origin are suitable candidates for treatment, such as, but not limited to, melanoma, small cell lung carcinoma, soft tissue sarcomas and neuroblastomas.

According to the invention, it is useful for the therapeutic agent to be targeted to the tumor site or the site of the malignancy or metastasis. Ig-fusion proteins containing antibodies directed toward antigens preferentially presented by tumors or malignant cells are particularly useful. For example, fusion proteins containing an antibody moiety with specificity for EpCAM (eg KS1/4), or embryonic Fibronectin (eg. BC1), or CEA, or chromatin complexes (eg. NHS76), or GD2 (eg 14.18), or CD19, or CD20, or CD52, or HER2/neu/c-erbB-2, or MUC-1, or PSMA are particularly useful. In addition, antibodies directed to various viral antigens are particularly useful.

EXAMPLES

Example 1

Construction of Ig-IL2 Fusion Genes with Codon Substitutions in the IL-2 Coding Sequence or in the Antibody Coding Sequence:

An expression vector for immunocytokines was described in Gillies et al., (1998) J. Immunol. 160:6195–6203. Several modifications in the nucleotide sequence enabled the addition of coding sequences to the 3' end of the human γ-1 gene. In the human γ-1 gene encoding the heavy chain, the XmaI restriction site located 280 bp upstream of the translation stop codon was destroyed by introducing a silent mutation (TCC to TCA). Another silent mutation (TCT to TCC) was introduced to the Ser codon three residues upstream of the C-terminal lysine of the heavy chain to create the sequence TCC CCG GGT AAA (SEQ ID NO. 4), which contains a new XmaI site [Lo et al., (1998) Protein Engineering 11:495–500].

The IL-2 cDNA was constructed by chemical synthesis and it contains a new and unique PvuII restriction site [Gillies et al., (1992) Proc. Natl. Acad. Sci. 89:1428–1432]. Both the XmaI and PvuII sites are unique in the expression vector, and they facilitated construction of antibody-IL2 variants, including the following.

1) huKS-ala-IL2. The construction of huKS-ala-IL2 has been described previously (e.g. WO01/58957). The resulting protein contains an amino acid substitution at the junction between the Ig heavy chain constant region and mature huIL-2. The junction normally has the sequence SPGK-APT (SEQ ID NO: 5) in which —SPGK- is the C-terminus of the heavy chain and —APT- the N-terminus of the mature IL-2 protein. In huKS-ala-IL2 a K to A substitution was introduced (referred to as position K[−1]) and the junction now has the sequence SPGA-APT (SEQ ID NO: 6). As a consequence the serum half-life of this protein is improved (see Example 5).

2) dI-KS-ala-IL2. This KS-IL2 fusion protein contains substitutions in KS-ala-IL2 to generate a version of the fusion protein in which potential T-cell epitopes have been eliminated (described in co-pending patent applications U.S. Ser. Nos. 10/112,582 and 10/138,727, the entire disclosures of which are incorporated by reference herein).

The constant region of the Ig portion of the fusion proteins of the invention may be selected from the constant region normally associated with the variable region, or a different constant region resulting in a fusion protein with the Ig portion including variable and constant regions from different subclasses of IgG molecules or different species. For example, the gamma4 constant region of IgG (SEQ ID NO: 7) may be used instead of gamma1 constant region (SEQ ID NO: 8). The alteration has the advantage that the gamma4 chain can result in a longer serum half-life. Accordingly, IgG gamma2 constant region (SEQ ID NO: 9) may also be used instead of IgG gamma1 constant region (SEQ ID NO: 8). In addition, the hinge region derived from IgG gamma1 (SEQ ID NO: 10) may replace the hinge region normally occurring in IgG gamma2 (SEQ ID NO: 11) or IgG gamma4 constant region (SEQ ID NO: 12). The Ig component of the fusion protein may also include mutations in the constant region such that the IgG has reduced binding affinity for at least one of FcγRI, FcγRII or FcγRIII. The fusion proteins of the invention may include mutations in the IgG constant regions to remove potential glycosylation sites and T-cell epitopes. For example, the various constant regions may include alterations in the C-terminal part of the constant regions to remove potential T-cell epitopes. For example, potential T-cell epitopes in the C-terminal part of various constant regions of IgG molecules are removed by changing the amino acid sequence KSLSLSPGK (SEQ ID NO: 13) in IgG gamma1 and IgG gamma 2 constant regions and amino acid sequence KSLSLSLGK (SEQ ID NO: 14) in IgG gamma4 constant region to amino acid sequence KSATATPGA (SEQ ID NO: 15).

3) huKS-ala-IL2(N88R). This huKS-IL2 variant contains the same amino acid substitution at the junction between the Ig heavy chain constant region and mature huIL-2 as described above (K[-1]A, created by the codon change AAA to GCC), and in addition it contains a substitution at position N88 in the sequence of mature huIL-2 in favor of R (created by codon change aAT to aGG). A further alteration was introduced into the nucleotide sequence of huIL-2 to eliminate an existing restriction site for Bam HI by introducing a silent mutation (amino acid position G98, the codon was switched from ggA tcc to ggC tcc).

A PCR-based mutagenesis strategy was used in the construction of huKS-ala-IL2(N88R). Two overlapping PCR fragments that span the coding sequence of the mature huIL2 were generated using huIL2 in a Bluescript vector (Stratagene) as a template. The upstream PCR fragment contained the nucleotide changes encoding K[-1]A and N88R by incorporating these mutations into the sense and antisense primers respectively. These changes are indicated by the bold nucleotides in the primer sequences. The sense primer sequence was: 5'CCCCGGGTGCCGCCCCAACT-TCAAGTTCTACA3' (SEQ ID NO: 16); the antisense primer sequence was: 5' AGCCCTTTAGTTCCAGAAC-TATTACGTTGATCCTGCTGATTAAGTCCCTAGGT 3'. (SEQ ID NO: 17). The underlined nucleotide represents a change that destroys the Bam HI site. The second, downstream PCR fragment contained a 20 nucleotide overlap region with the upstream PCR fragment and the remaining IL2 sequence. The sense primer used in this reaction was 5' AGTTCTGGAACTAAAGGGCTCCGAAACAACATTC-ATGTGT (SEQ ID NO: 18). Again, the underlined nucleotide denotes the silent mutation that destroys the Bam HI site. The antisense primer used was the standard M13 reverse primer that anneals to a sequence in the pBluescript vector. These overlapping PCR fragments were used in a reaction with the primer in SEQ ID 16 and an M13 reverse primer to generate the final PCR product, which was subsequently inserted into a TA vector (Invitrogen).

The sequence of the inserted fragment was verified, and a 442 bp Xma I/Xho I fragment containing the modified IL2 sequence (from plasmid TA-IL2(N88R)) was used to replace the wild-type huIL-2 sequence in the parental immunocytokine expression plasmid (encoding huKS-IL2). The resultant immunocytokine expression plasmid encoding huKS-ala-IL2(N88R) was verified by restriction mapping and sequencing.

4) huKS M1-IL2(TTSR (SEQ ID NO: 19)). The immunocytokine variant huKS M1-IL2 was constructed by standard recombinant DNA techniques (and described e.g. in co-pending patent application U.S. Ser. No. 10/112,582, the entire disclosure of which is incorporated by reference herein). It contains multiple amino acid substitutions in the antibody—IL-2 junction region of the fusion protein, which eliminate potential T-cell epitopes and results in a less immunogenic protein. The sequence was changed from KS LSLSPGA-APT (SEQ ID NO: 20) to KSATATPGA-APT (SEQ ID NO: 21) (the dash denotes the Ig/IL-2 junction site and substituted amino acids are underlined) and is denoted as "M1". Also incorporated in this variant is the K to A change at the last amino acid before the junction that has been shown to increase serum half-life of the immunocytokine.

huKS M1-IL2(TTSR) contains further amino acid substitutions located in the IL-2 portion of the immunocytokine. To eliminate potential T-cell epitopes created by the substitution of N88R described above, the sequence is changed from —DLISNI-(SEQ ID NO: 22) of the natural huIL-2 to —DTTSRI-(SEQ ID NO: 23).

A PCR based mutagenesis approach was used to introduce the changes into the nucleotide sequence of the huIL-2 gene, by incorporating the mutations into the sense primer. The sequence TTxR was created by codon changes ACC, ACC and AGG respectively. A mutagenized 197 bp PCR fragment encompassing the 3' end of the hu IL-2 sequence was generated from the template immunocytokine expression plasmid encoding huKS-ala-IL2(N88R) using a sense primer of the sequence 5' ACTTAAGACCTAGGGACAC-CACCAGCAGGATCAACGTAATAGT3' (SEQ ID NO: 24) and an antisense primer of the sequence 5' ATCATGTCTG-GATCCCTC3' (SEQ ID NO: 25). The PCR fragment was cloned into a TA vector and the sequence verified. To regenerate the complete IL-2 sequence this fragment was ligated as a Afl II/Xho I restriction digest to a 2 kb Hind III/ Afl II fragment obtained from immunocytokine expression plasmid encoding huKS-ala-IL2(N88R) and inserted into a Hind III/Xho I restricted pBluescript vector. The mutagenized IL-2 gene was then exchanged in place of the natural huIL-2 sequence in an immunocytokine expression plasmid encoding for KS M1-IL2 in a three-way ligation.

5) huKS(N to Q)-IL2. An immunocytokine expression plasmid encoding huKS(N to Q)-IL2 was constructed using standard recombinant DNA techniques. huKS(N to Q)-IL2 contains an amino acid substitution in the CH2 domain of the antibody Fc gamma 1 constant region that eliminates N-linked glycosylation. The amino acid sequence is changed from QYNSTYR (SEQ ID NO: 1) to QYQSTYR (SEQ ID NO: 26), with the substituted amino acid indicated in bold. Similarly, fusion proteins including gamma 2 and gamma 4 constant regions were constructed that contain mutations that change the amino acid sequence QFNST (SEQ ID NO: 2) to QAQST (SEQ ID NO: 27), thereby additionally eliminating a potential T cell epitope.

Example 2

Chemical or Enzymatic Modifications of an Ig-IL2 Fusion Protein Leading to Modified Receptor Specificity:

This example describes biochemical manipulations of the immunocytokine used to generate a PEGylated huKS-IL2 or to a deglycosylated huKS-IL2, and variants thereof. The same methods can be applied to other IL-2 fusion proteins, such as the immunocytokine 14.18-IL2 or albumin-cytokine fusions. These variants were used in a subsequent example to investigate their effect on the proliferative response of various cell lines in a cell based bioassay (Table 1) or on the pharmacokinetic properties of the molecule.

PEGylation of huKS-IL2. PEG (20,000) was covalently attached to the protein via amine groups present on the protein. For this purpose a reactive derivative of PEG containing a succinimide linker (mPEG-Succinimidyl Propionate, termed "SPA-PEG" below) was employed. huKS-IL2 was extensively dialyzed in an amine-free buffer composed of 50 mM Sodium Phosphate (pH 7.5), 0.05% Tween 80, and concentrated. Excess SPA-PEG was combined with huKS-IL2 at a molar ratio of either 5:1 or 10:1. Immediately before use, a 5 mM SPA-PEG stock solution was prepared in deionized water. An appropriate volume of the SPA-PEG solution was combined with huKS-IL2 and the reaction was incubated on a rocking platform for 30 to 40 minutes at room temperature. A 5 to 10 molar excess of glycine was added to quench the reaction, and the reaction products were purified by size exclusion chromatography. A Superdex 200 column, equilibrated in 50 mM HEPES and 150 mM NaCl, was loaded with the reaction sample and eluting fractions containing the PEGylated protein were pooled and concentrated.

N-Glycanase treatment of huKS-IL2. huKS-IL2 (1.5 mg) was incubated with 30 mU PNGaseF (New England Biolabs) overnight at 37° C. The reaction product was purified by passage over a ProteinA-Sepharose column and elution of the bound huKS-IL2 at pH 3. The eluate was neutralized and concentrated in a spin column in a buffer of PBS and 0.05% Tween 80. Deglycosylation of huKS-IL2 was verified be size exclusion chromatography and on a urea gel.

Example 3

Expression and Purification of Ig-IL2 and Ig-IL2 Variants

The general procedure described here for huKS-ala-IL2 (N88R) may be used for a wide variety of Ig-cytokine fusion proteins, including Ig-fusions to mutant cytokines. To obtain stably transfected clones which express huKS-ala-IL2 (N88R), DNA of the immunocytokine expression plasmid encoding huKS-ala-IL2(N88R) was introduced into the mouse myeloma NS/0 cells by electroporation. NS/0 cells were grown in Dulbecco's modified Eagle's medium supplemented with 10% heat-inactivated fetal bovine serum, 2 mM glutamine and penicillin/streptomycin. About $5 \times 10^6$ cells were washed once with PBS and resuspended in 0.5 ml PBS. 10 μg of linearized plasmid DNA were then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 μF. Cells were allowed to recover for 10 min on ice, after which they were resuspended in growth medium and plated onto two 96 well plates. Stably transfected clones were selected by growth in the presence of 100 nM methotrexate (MTX), which was added to the growth medium two days post-transfection. The cells were fed every 3 days for two to three more times, and MTX-resistant clones appeared in 2 to 3 weeks. Supernatants from clones were assayed by anti-Fc ELISA to identify high producers. High producing clones were isolated and propagated in growth medium containing 100 nM MTX.

The immunocytokine was purified from the tissue culture supernatant by Protein A affinity column chromatography. For huKS-ala-IL2(N88R), a recombinant Protein A (rPA) Agarose column was pre-equilibrated with ten volumes of running buffer, such as 100 mM Arginine, 5 mM Citrate, 0.01% Tween 80 pH 5.6, and the column was loaded with filtered cell culture supernatant containing huKS-ala-IL2 (N88R) at 16 ml/min to a binding of approximately 40 mg/ml of rPA resin. The column was washed extensively with the same buffer and finally the immunocytokine was eluted in 50 mM glycine at pH 3. Peak fractions were collected and pH was adjusted to neutral with 1 N NaOH.

Example 4

Activity of Ig-IL2 Variants in Bioassays.

For cell based bioassays, cell lines that depend on IL-2 for growth were utilized and the activity of Ig-fusion proteins, for example huKS-IL2 and huKS-IL2 variants, was assessed by proliferation of these cells. For instance, CTLL-2 (ATCC# TIB-214; Matesanz and Alcina, 1996) and TF-1β (Farner et al., [1995] Blood 86:4568–4578) were used to follow a T cell response and an NK cell-like response, respectively. CTLL-2 is a murine T lymphoblast cell line that expresses the high affinity IL-2Rαβγ, and TF-1β is a human cell line derived from immature precursor erythroid cells that express the intermediate affinity IL-2Rβγ. Another useful cell line for these assays is, for example, the cell line derived from human adult T cell lymphoma Kit-225 (K6) (Uchida et al., [1987] Blood 70:1069–1072). When paired with cell line TF-1β, the activity of the fusion proteins is evaluated in a pair of cell lines harboring receptors of the same mammalian species. These assays may also be performed with cell populations derived from human PBMCs (Peripheral Blood Mononuclear Cells), either to isolate NK-cells, which bear IL-2Rβγ, or to produce activated T cells, which express IL-2Rαβγ. Techniques to isolate these cell populations from hu PBMCs are known to those of ordinary skill in the art. For example, T cells, or PHA-blasts, are obtained by incubating PBMCs for three days in 10 microgram/ml of phytohemagglutinin (PHA-P; L9017, Sigma, St. Louis). Resting NK cells are commonly obtained by a negative selection protocol, for instance using an NK-cell isolation kit (Miltenyi Biotec, Auburn, Calif.) for human cells. To correlate the activity of these fusion proteins with results obtained from mouse tumor models, it is also useful to perform these assays on cell populations obtained from the mouse expressing one or the other IL-2 receptor complex. For example, an NK cell population may be obtained from spleens of recombinant-deficient (SCID) Balb/C mice using a SPINSEP™ murine NK-cell enrichment kit (Stemcell Technologies Inc, Vancouver, BC, Canada). The purity of any of these enriched populations can be assessed by FACS analysis.

Briefly, washed cells were plated at a density of 10,000 cells/well in a 96 well microtiter plate and incubated in cell medium supplemented with, for example, purified huKS-IL2 or huKS-IL2 variants. In addition, wild type huIL-2 protein, obtained from R&D Systems (Minneapolis, Minn.) was assayed as a standard. The added protein was prepared as a dilution series over a roughly 1000-fold concentration range between 0.45 ng/ml and 420 ng/ml (normalized with respect to molar equivalents of IL2). After 32 hours, 0.3 μCi of [methyl-3H]thymidine (Dupont-NEN-027) was added to each well and cells were incubated an additional 16 hours. Cells were then harvested and lysed onto glass filters. 3H-thymidine incorporated into DNA was measured in a scintillation counter.

An ED50 value for each huKS-IL2 protein variant with respect to cell proliferation was obtained from plotting a dose response curve and identifying the protein concentration that resulted in half-maximal response. The selectivity of the response was expressed as a ratio of ED50 values for example, ED50 [TF1-β]/ED50 [CTLL-2]. Thus, a high ED50 ratio indicated that a relatively higher dose of the protein was required to elicit a TF-1β cell response as compared to a CTLL-2 cell response. The ratio of the ED50 values of the huKS-IL2 variants was compared to free huIL-2 and the parental huKS-IL2 proteins. This normalized value is a measure of the differential effect. A value larger than the one obtained for the reference protein indicated a shift in selectivity toward CTLL-2 cells. In some cases it may be preferable to obtain ED50 ratios with cell lines that originate from the same species, so that IL-2 activities are not additionally influenced by cross-species differences in their interaction with the receptors. The following example uses murine CTLL-2 and human TF-1β cells to calculate ED50 ratios with Ig-IL2 fusion proteins and free IL-2, and representative results from such an experiment are shown in Table 1.

TABLE 1

| Protein | ED50 Ratio |
| --- | --- |
| IL-2 | 0.81 |
| HuKS-IL2 | 0.11 |
| HuKS-ala-IL2 | 0.17 |
| KS(NtoQ)-IL2 | 0.72 |
| HuKS-ala-IL2(N88R) | 2300 |
| KS-IL2(TTSR) | >6 |
| HuKS-IL2 PEGylated | 1.99 |
| HuKS-IL2 + Glycanase | 0.45 |
| 14.18-IL2 | 0.07 |
| 14.18-IL2 PEGylated | 1.34 |
| 14.18-IL2 + Glycanase | 0.21 |

In this example, compared with the ED50 ratio obtained with free IL-2 (0.81), an approximately 5-fold lower ED50 ratio was obtained with huKS-IL2 (0.17). This indicated that the fusion protein was shifted in its selectivity profile, displaying a greater selectivity towards TF-1β cells. A different antibody/IL-2 combination, 14.18-IL2, also was more selective for TF1-β than IL-2 alone (ED50 ratio of 0.07), indicating that this effect was not limited to a specific antibody contained in the antibody-IL2 fusion protein, and the reduced activity of human Ig-IL2 fusion proteins towards murine high affinity receptor bearing cells relative to huIL-2 may reflect a general feature of the Ig-IL2 fusion proteins.

Other variants had an altered ED50 ratio such that a CTLL-2 cell response was favored. A dramatic effect was seen with huKS-ala-IL2(N88R), for which the ED50 ratio was greater than 2000, reflecting that TF-1β cell proliferation, mediated in these cells by the intermediate affinity receptor, was barely detectable. Thus, while huKS-ala-IL2(N88R) activated signaling of cells with IL-2Rαβγ, it did not significantly activate cells with IL-2Rβγ. The activity of huKS-ala-IL2(N88R) could also be assayed on purified murine NK cells expressing the murine IL-2Rβγ complex; in contrast to what was reported for the free human IL2(N88R) protein—which indicated that the selectivity was virtually lost when mouse T and NK cells were examined (see Wetzel et al., ASCO 2001 Meeting Abstract)—the ED50 value for huKS-ala-IL2(N88R) in the mouse NK cells was similar to that observed with TF-1β cells.

Subtle shifts in the selectivity of the response towards CTLL-2 cells were observed in Ig-IL2 variants with alterations that affect glycosylation of the antibody portion of the fusion protein. Specifically, KS(NtoQ)-IL2, which lacks a glycosylation site in the Fc portion of the antibody, displayed a 3-fold increase in ED50 Ratio (0.72) relative to huKS-IL2, whereas N-Glycanase treated huKS-IL2 displayed a 2-fold increase (ED50 ratio of 0.45) relative to huKS-IL2. Likewise, N-Glycanase treatment of IL-2 fused to a different antibody molecule lead to a similar result; for instance, N-Glycanase treated 14.18-IL2 gave a 3-fold increase in the ED50 ratio as compared to untreated 14.18-IL2. These results indicated that certain alterations in the antibody portion of the molecule itself affect the binding and activation properties of an IL-2 molecule fused to it.

PEGylation of the fusion protein also altered its selectivity profile. Again, a shift towards CTLL-2 stimulatory activity was observed. For huKS-IL2, a PEGylated variant resulted in a 9-fold increase in selectivity in favor of CTLL-2 cells (ED50 ratio of 1.99), and for 14.18-IL2 a 20-fold increase was induced by PEGylation (ED50 ratio of 1.34).

In some instances, these shifts in selectivity for a given protein may also reflect the particular combination of cell types employed in the assays, as illustrated in representative results shown in Table 2. For example, when KS-IL2, KS-ala-IL2 and IL-2 were compared using the human IL-2Rαβγ bearing cell line Kit 225 instead of murine CTLL-2, the patterns of shift in selectivity was not maintained. Particularly with regards to Kit 225 cells, these three proteins exhibited essentially identical activity. Mostly however, the trends in the selectivity response of Ig-IL2 variants between TF-1β cells and Kit-225 cells were found to be similar to those established with TF-1β cells and CTLL-2 cells, including the effect of deglycosylation of the Fc-moiety of a Ig-IL2 fusion protein (see representative results in Table 2 below and Example 10).

TABLE 2

| Protein | ED50 Ratio TF-1β/Kit-225 |
| --- | --- |
| IL-2 | 2.8 |
| HuKS-IL2 | 4 |
| HuKS-ala-IL2 | 10.4 |
| KS-ala-IL2(N88R) | 52,000 |

In addition, it was found that Kit-225 cells were more sensitive to IL-2 and IL-2 fusion proteins and variants thereof than CTLL-2 cells. For example, the ED50 value for huKS-ala-IL2 was 0.08 in Kit-225 cells and 5.0 in CTLL-2 cells, and for KS-ala-IL2(N88R) it was 0.13 in Kit 225 cells and 3 in CTLL-2 cells, indicating an approximately 10–50 fold increase in sensitivity of Kit 225 cells in these assays. Thus the value of the ED50 ratio for a given protein is dependent on the particular combination of cell types employed.

Example 5

Figure 2:
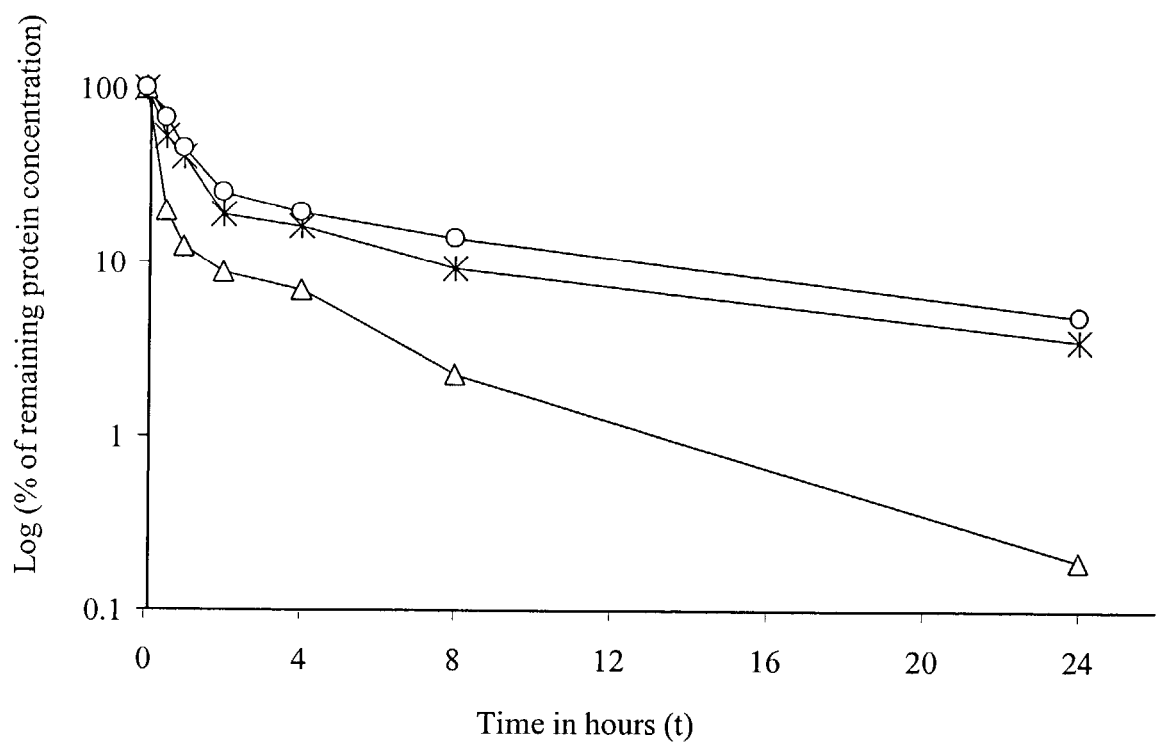
FIG. 2 shows typical pharmacokinetic profiles of the fusion protein immunocytokine huKS-IL2 (represented by triangles) and two variants, huKS-ala-IL2 (represented by circles) and huKS-ala-IL2(N88R) (represented by stars).

Pharmacokinetics of IL-2 Fusion Proteins with Modified Receptor Binding Characteristics The pharmacokinetic (PK) profile of huKS-ala-IL2 (N88R) was compared to the profile of huKS-ala-IL2 and huKS-IL2. For each protein, three 6–8 week old mice were used. Twenty five µg of the fusion proteins, diluted to 125 µg/ml in PBS, were injected in the tail vein of mice, and 50 µl blood samples were obtained by retro-orbital bleeding immediately after injection (0 hrs) and at 0.5, 1, 2, 4, 8, and 24 hrs post injection. Blood samples were collected in heparin-coated tubes to prevent blood clotting, and immunocytokine levels in the post-cellular plasma supernatant were measured in an ELISA assay. The procedure of the ELISA assay used for pharmacokinetic studies has been previously described (WO01/58957). This assay measured the presence of an intact immunocytokine. Capture of the immunocytokine from plasma was carried out on EpCAM-coated plates and the detection was performed with an HRP-conjugated antibody directed against IL-2. It had been shown previously that the huKS-IL2 variant with a K to A substitution in the junction, huKS-ala-IL2, had a dramatic improvement in circulating half-life as compared to huKS-IL2 (WO01/58957). In fact, the circulating half-life of huKS-ala-IL2(N88R) was found to be similarly improved, indicating that the N88R alteration in the IL-2 portion of the molecule had no substantial effect on the pharmacokinetics. Results of a representative experiment are shown in FIG. 2. FIG. 2 illustrates a time course of the concentration of the immunocytokine present in the serum (expressed as a percentage of the protein concentration remaining in the serum relative to the starting concentration present immediately after intravenous administration) over 24 hours. Protein concentrations are determined in an ELISA assay in which the immunocytokine is captured by its antibody moiety and detected by its cytokine moiety. X-axis=time t in hours; Y-axis=log(% of remaining protein concentration).

Example 6

Toxicity of Ig-IL2 Fusion Proteins with Modified Receptor Binding Characteristics in a Mammal The relative toxicity of the KS-IL2 variants huKS-IL2, huKS-ala-IL2, and huKS-ala-IL2(N88R) in mice was examined. As was shown in Example 5, huKS-ala-IL2 and huKS-ala-IL2(N88R) have substantially increased PK when compared to huKS-IL2. Nonetheless, for comparison purposes, an identical dosing schedule was used for the different molecules despite the difference in PK. While a longer serum half-life is likely to increase the efficacy of a therapeutic it may also lead to increased toxicity. Yet this example shows that, while huKS-ala-IL2 had increased toxicity compared to huKS-IL2 (because of a longer circulating half-life), huKS-ala-IL2(N88R) had decreased toxicity compared to huKS-IL2 despite a longer circulating half-life.

Balb/C mice (3 animals per experimental condition) were given daily intravenous injections of one of three proteins for five consecutive days. The fusion proteins were diluted into 200 μl of PBS and were administered at the following dosage: huKS-IL2 and huKS-ala-IL2 at 25, 50, or 75 μg per mouse, and huKS-ala-IL2(N88R) at 50, 75, or 100 μg per mouse. A control group received intravenous injections of PBS. Survival of the mice was monitored daily and the effect on mouse survival was examined. Mice survived administration of all doses of huKS-IL2. huKS-ala-IL2, however, was more toxic. While the mice tolerated a dose of 25 μg of huKS-ala-IL2, all 3 mice died on day 6 at a dose of 50 μg, and at a dose of 75 μg, two mice had died at day 4.5, and the third mouse at day 5. huKS-ala-IL2(N88R), on the other hand, was well tolerated at all doses, including 100 μg. Indeed, huKS-ala-IL2(N88R) was also administered at a dose of 200 μg per mouse, and the mice survived. Thus, huKS-ala-IL2(N88R) was significantly less toxic than huKS-ala-IL2.

Mice that had died during the course of the treatment with huKS-ala-IL2 were dissected and their organs evaluated. All organs, including lung, spleen, liver, stomach, and kidney were grossly distended, indicative of extensive vascular leakage. Organs of animals treated with variant huKS-ala-IL2(N88R) were also evaluated. Mice were treated as described above, and it was found that organ weights from huKS-ala-IL2(N88R)-treated animals were generally similar to those of control animals, particularly for the lungs and liver. Without wishing to be being bound by theory, it is thought that the increase in the weight of the spleen is more due to an increase in cellularity caused by an antibody immune response against this human protein rather than a vascular leak. It is inferred that huKS-ala-IL2(N88R) produces less severe vascular leaks than huKS-ala-IL2. Table 3 provides an example of approximate values for the x-fold increase in organ weight relative to organs of a control mouse:

TABLE 3

| ORGAN | WEIGHT INCREASE (x fold) | |
|---|---|---|
| | HuKS-ala-IL2 (20 μg/mouse) | huKS-ala-IL2(N88R) (100 μg/mouse) |
| Lung | 4 | 1.7 |
| Spleen | 3 | 3 |
| Liver | 1.5 | 1 |
| Kidney | 1 | 1 |

The effect of various mouse strain backgrounds, with known alterations in their immune system make-up, was evaluated with respect to the toxicity of these Ig-IL2 fusion proteins. Mouse strains DBA/2, Balb/C, B6.CB17-Prkdc$^{scid}$/SzJ (SCID), beige, and SCID/beige were used. The fusion proteins were administered as above at a dose of 25 μg and 50 μg per mouse for huKS-ala-IL2 and at a dose of 200 μg per mouse for huKS-ala-IL2(N88R), and mouse survival and weight was assessed over a two week period.

In the case of huKS-ala-IL2, most mice strains gave results similar to those seen with Balb/C mice reported above: the dose of 50 μg led to animal death at day 5, whereas at the lower dose the animals survived and their weights recovered to about their initial weight but did not reach the weight gains of the mock-treated control animals. Interestingly, beige mice, deficient in functional NK cells, were better able to tolerate the high dose of 50 μg; two animals had died by day 9, but one, while it initially lost significant weight (around 25% by day 7), recovered, and by day 15 had attained the body weight of mock-treated animals and those treated at the lower dose. DBA/2 mice were more sensitive to huKS-ala-IL2; even at the lower dose, DBA/2 animals died at day 5 and day 9.

With huKS-ala-IL2(N88R), the increased susceptibility of DBA/2 mice to Ig-IL2 fusion proteins was also apparent: by day 8, all animals had died, and even at half the dose (100 μg) the animals had died by day 9. Again, the fusion protein was best tolerated in beige mice, whereas the SCID/beige mice lost significant weight (remained stable at around 80% of mock-treated control by day 10).

Example 7

Efficacy of an Ig-IL2 Fusion Protein with Modified Receptor Binding Characteristics in Treatment of Various Tumors in a Mammal a) Treatment of a CT26/KSA subcutaneous tumor in Balb/C mice. CT26 colon carcinoma cells, transduced with the gene encoding human KS antigen (KSA), were used to induce a subcutaneous tumor. 2×10E$^6$ viable cells were suspended in 100 μl of PBS and injected subcutaneously into the dorsa of 6 week old Balb/C mice. When tumor size reached 100–200 mm$^3$, groups of 8 mice were subjected to one of three treatment conditions: on five consecutive days, intravenous injections with 15 µg of either huKS-ala-IL2 or of huKS-ala-IL2(N88R) diluted into 200 µl of PBS, or PBS alone, were administered. Disease progression was evaluated by measuring tumor volume twice a week for 50 days. In the control animals, tumor volume increased steadily, reaching approximately 3500 to 6000 mm$^3$ in size at the time of sacrifice, which was around day 32. By contrast, tumor volumes for both experimental groups remained essentially constant up to 50 days, indicating that huKS-ala-IL2(N88R) was as effective as huKS-ala-IL2 in preventing tumor growth.

b) Treatment of a LLC/KSA subcutaneous tumor in C57BL/6 mice. In a second tumor model, a subcutaneous tumor was induced using Lewis Lung Carcinoma cells transduced with the gene encoding the KS antigen. 1×10E6 viable LLC cells expressing EpCAM were suspended in 100 µl of PBS and injected subcutaneously into the dorsa of 6–8 week old C57BL/6 mice. When tumor size reached 100–150 mm$^3$, groups of eight mice were treated and evaluated as above, except that administered dose was increased to 20 µg per injection. In the control animals, tumor volume increased rapidly, exceeding 6500 mm$^3$ in 20 days; the growth of the tumor for both experimental conditions was retarded to the same extent, reaching 4000 mm$^3$ over the same period, indicating again that there was no difference in efficacy between treatment with huKS-ala-IL2 and huKS-ala-IL2(N88R) at the same dose.

c) Treatment of a LLC/KSA subcutaneous tumor in B6.CB17-Prkdc$^{scid}$/SzJ mice. The fusion proteins of the invention may also be effective on cells other than mature T cells. For example, in one experiment, the fusion proteins of the invention led to retardation of tumor growth even in mice that lack mature T-cells. These results suggest that the fusion proteins of the invention may be useful in the treatment of tumors in, for example, immunocompromised patients.

An LLC/KSA subcutaneous tumor model was evaluated in 11 week old B6.CB17-Prkd$_{scid}$/SzJ mice, which are compromised in their T-cell and B-cell mediated immune response. The same treatment protocol as described above was followed. Tumors in the control animals grew rapidly, to 3500 mm$^3$ in 15 days. Both huKS-ala-IL2 and huKS-ala-IL2(N88R) were similarly effective in retarding tumor growth to less than half that size over the same period. Moreover, the differences in tumor growth rates between the C57BL/6 mice, which have an intact immune system, and the B6.CB17-Prkdc$^{scid}$/SzJ mice, which lack T cells and B cells, were minimal.

Furthermore, the fact that KS-ala-IL2 led to the treatment of the tumor equally well in mice with an intact immune system and in mice lacking functional T cells, indicated that in this tumor model the immunologic response operated through a non-T cell mediated mechanism. Therefore, it is valuable to maintain in a therapeutic molecule the option to stimulate an immunologic response through a variety of effector cells. In the case of KS-ala-IL2(N88R), which was as effective as KS-ala-IL2 in either mouse background, effector cell activities that act independently of T cells were apparently preserved.

d) Treatment of LLC/KSA metastases to the lungs of C57BL/6 mice. LLC/KSA cells were also used in a lung metastasis model. 10×10E6 viable cells were suspended in 200 µl PBS and injected intravenously into 6–8 week old C57BL/6 mice. On day 4, groups of eight mice were subjected to one of the following treatment conditions: on five consecutive days, the mice were injected intravenously with 200 µl PBS, or with 20 µg of either KS-ala-IL2 or KS-ala-IL2(N88R) diluted into 200 µl of PBS. The animals were sacrificed at about day 27, and lungs were dissected and fixed in Bouin's solution. The extent of metastasis in the lungs was evaluated by scoring the percentage of surface area covered by metastasis and by lung weight.

Lungs of the control group had over 96% of their surface area covered by metastases, and approximately a five-fold increase in lung weight (0.75 g) over a normal lung. By contrast, lungs of mice treated with huKS-ala-IL2 were minimally covered with metastases (5.6%), and those of mice treated with huKS-ala-IL2(N88R) were virtually free of metastases (0%). Lungs of animals treated with huKS-ala-IL2 and huKS-ala-IL2(N88R) were of normal weight. Thus, huKS-ala-IL2(N88R) proved as efficacious as huKS-ala-IL2 in treating the lung metastases at a dose many fold lower than the threshold that would affect their survival.

Example 8

KS-IL2 Variants in Combination Therapy

The effect of administering a low toxicity KS-IL2 variant, such as huKS-ala-IL2(N88R), in conjunction with a second immuno-modulatory agent for the treatment of tumors was investigated, employing the subcutaneous tumor model LLC/KSA in mice as described in Example 7b.

a) huKS-ala-IL2 variants and cyclophosphamide. For the combination therapy, cyclophosphamide was administered intraperitoneally at a dose of 75 mg/kg on day 0, at which point the tumors averaged 90 mm$^3$, and was followed by a daily administration of the fusion protein over five days (on day 1 through day 5). huKS-ala-IL2(N88R) was administered at either a 20 µg or a 100 µg dose. Control conditions included mock-treated animals and animals treated either with huKS-ala-IL2 alone at a 20 µg dose, or with huKS-ala-IL2(N88R) alone at a 20 µg or a 100 µg dose. Tumors in mock-treated animals had progressed to about 5000 mm$^3$ by day 19, whereas tumors of mice treated with huKS-ala-IL2 were around 2200 mm$^3$, and of mice treated with 20 µg or 100 µg of huKS-ala-IL2(N88R) were around 2600 mm$^3$ and 1700 mm$^3$ respectively. Co-administration of cyclophosphamide resulted in a tumor of 1700 mm$^3$ at the 20 µg dose of huKS-ala-IL2(N88R) and of 1250 mm$^3$ at the higher dose, significantly smaller than the treatment with huKS-ala-IL2 alone.

b) huKS-ala-IL2 variants and indomethacin. For the combination therapy, indomethacin was administered orally at a dose of 35 µg/mouse/day along with a daily administration of the fusion protein over five days (day 1 through day 5). Tumors initially averaged 90 mm$^3$. huKS-ala-IL2(N88R) was administered at a 20 µg dose. Control conditions included mock-treated animals and animals treated either with huKS-ala-IL2 alone at a 20 µg dose, or with huKS-ala-IL2(N88R) alone at a 20 µg dose. Tumors in mock-treated animals had progressed to about 5000 mm$^3$ by day 19, whereas tumors of mice treated with huKS-ala-IL2 were around 2200 mm$^3$, and of mice treated with 20 µg of huKS-ala-IL2(N88R) were around 2600 mm$^3$ and 1700 mm$^3$ respectively. Co-administration of indomethacin resulted in a decrease in tumor size to 850 mm$^3$ at the 20 µg dose of huKS-ala-IL2(N88R), a significantly smaller tumor than obtained by treatment with huKS-ala-IL2 alone.

Example 9

KS-IL2 Variants with an Improved Therapeutic Index.

KS-IL2 variants are constructed with mutations at particular positions in the IL-2 sequence. For example, substitutions are created at positions that are likely to interface with the α subunit of IL-2 receptor. A suitable residue is, for example, F42 in the mature sequence of huIL-2. The aromatic ring structure of this amino acid is thought to stabilize the local conformation in IL-2 (Mott et al, JMB 1995, 247:979), and it is found that substitutions at this position with for instance Y, A or K in the immunocytokine lead to a molecule with progressively decreased IL-2 receptor affinity and bioactivity. These molecules are tested in animals and it is found that an increase in the therapeutic index in the treatment of tumors is achieved when compared with the unaltered form of the immunocytokine. Other substitutions that are effective are at positions R38 and K43.

Other substitutions in the IL-2 portion of the immunocytokine are in a region that is likely to interface with the β subunit, for example, at position E15 or L19 of the mature hu IL-2. When these residues are mutated to, for example, A or R in the immunocytokine it is found that the variant immunocytokines have a decreased affinity for the β subunit of the IL-2 receptor as compared to the unaltered form of the immunocytokine. It is generally found that the effects with substitutions to R are more severe than with substitutions to A, which may be related to the bulkiness of the side chain of R. These molecules are tested in animals and it is found that an increase in therapeutic index in the treatment of tumors is achieved when compared to the unaltered form of the immunocytokine. Other substitutions are introduced at positions D84 and V91 and are shown also to be effective in increasing the therapeutic index.

A substitution in the IL-2 portion of the immunocytokine that is likely to affect a region of the molecule that interfaces with the γ subunit of the IL-2 receptor is introduced at position N119 of the mature hu IL-2. A more subtle immunocytokine variant is created with a mutation to A and a more disruptive mutation is created with a mutation to R. The effect of these variants is tested in animals bearing tumors and it is found that these variant immunocytokines do have an improved therapeutic index as compared to the unaltered form of the immunocytokine.

It is also found that an increase in therapeutic index can be achieved by generating multiple mutations in the IL-2 immunocytokine, particularly for molecules where single mutations in the immunocytokine have shown only a marginal or negligible increase in therapeutic index. For example, an immunocytokine containing the combination F42A with L19A, or L19A with N119A, is found to be more effective than either immunocytokine variant alone. For an application involving multiple mutations, it is particularly useful to use mutations that decrease the size of an amino acid side chain. Another substitution introduced into the IL-2 portion of the immunocytokine is at T51 of the mature huIL-2. Whereas a mutation to A does not show an improvement in therapeutic index, the mutation to P creates an immunocytokine with improved therapeutic index when compared to the unaltered form of the immunocytokine in the treatment of tumors.

Example 10

Ig-IL2 Fusion Protein Variant huKS-ala-IL2(D20T) and Derivatives Thereof

Variants based on Ig-IL2(D20T), which contains the substitution of an aspartate to a threonine at position 20 of the mature huIL-2, were generated. These variants contain additional substitutions in the Ig domain, such as in the Fc portion or in the antibody targeting domains. To generate the DNA constructs encoding these molecules, procedures were followed essentially as described in Example 1, using a PCR approach with construct-specific primers to introduce the mutation and appropriate cloning strategies, familiar to those reasonably skilled in the art.

a) huKS-ala-IL2(D20T). To introduce the mutation D20T, a PCR mutagenesis approach was used with the primer set 5'-CAGCTGCAACTGGAGCATCTCCTGCTGACCCT-CCAGATGATTCTGAAT-3' (the bold nucleotides indicating the substituted codon) (SEQ ID NO: 28) and primer T3 (5'-ATTAACCCTCACTAAAGGGA-3') (SEQ ID NO: 29), the DNA fragment was amplified from wild-type huIL-2 DNA on a pBS plasmid and inserted into a TA vector (Invitrogen) to generate TA-IL2(D20T). Mutagenesis was verified by sequencing. To substitute for the original IL-2 sequence in huKS-ala-IL2, a 385 bp PvuII/XhoI fragment from TA-IL2(D20T) was cloned into the parental immunocytokine plasmid in a triple ligation reaction. The fusion protein was expressed and purified essentially as described in Example 3. Amino acid sequences corresponding to hu-KS heavy and light chain variable regions are shown in SEQ ID NOs: 30 and 31 respectively.

Further variants of huKS-ala-IL2(D20T) were generated, incorporating the same PCR-derived fragment into different plasmid back-bones.

b) dI-KS-ala-IL2(D20T). A version of KS-ala-IL2 with an alteration removing a potential T-cell epitope has been previously described. The fusion protein was expressed and purified essentially as described in Example 3. The amino acid sequence corresponding to the heavy chain of the dI-KS antibody fused to the IL2(D20T) variant is depicted in SEQ ID NO: 32. SEQ ID NO: 33 and 34 correspond to the dI-KS heavy chain and light chain variable regions respectively.

c) De-glycosylated dI-KS-ala-IL2(D20T). Enzymatic deglycosylation using N-Glycanase was performed on the protein dI-KS-ala-IL2(D20T) essentially as described in Example 2.

d) dI-KS(γ4h)(FN>AQ)-ala-IL2(D20T). The Ig-moiety for this IL-2(D20T) fusion protein was derived from the constant region of an IgG γ4 subclass (SEQ ID NO: 7), which in addition retained features of the IgG γ1 hinge (SEQ ID NO: 10). Furthermore, mutations that remove potential T-cell epitopes were introduced. Additionally, this fusion protein contains the substitution from asparagine to glutamine, which eliminates the N-glycosylation site in Fc (see Example 4). The concomitant substitution of a phenylalanine to alanine removes the potential T-cell epitope. The fusion protein was expressed and purified essentially as described in Example 3.

e) dI-NHS76(γ2h)-ala-IL2(D20T). The Ig-moiety for this IL-2(D20T) fusion protein was derived from the constant region of an IgG γ2 subclass, which in addition retained features of the IgG γ1 hinge. In NHS76, the Ig variable regions are directed against epitopes contained in DNA-histone complexes and specifically recognize necrotic centers of tumors (Williams et al, PCT WO 00/01822). Also, a mutation that eliminates a potential T-cell epitope in the variable region of the light chain was introduced. This residue, leucine 104, lies at the CDR3 V-J junction, and was substituted by a valine. The fusion protein was expressed and purified essentially as described in Example 3.

f) dI-NHS76(γ2h)(FN>AQ)-ala-IL2(D20T). This protein, based on the protein of Example 10e, additionally contains the mutations that eliminate N-linked glycosylation in Fc and a potential T-cell epitope, as described in Example 10d. The fusion protein was expressed and purified essentially as described in Example 3. In one embodiment, fusion proteins of the invention include the heavy chain sequence of the NHS76(γ2h)(FN>AQ) molecule fused to the IL2(D20T) variant, as depicted in SEQ ID NO: 35, and the light chain variable and constant region sequence corresponding to SEQ ID NO: 36. However, the heavy chain region of SEQ ID NO: 35 can be used in combination with any IgG light chain variable or constant region.

g) dI-NHS76(γ4h)-ala-IL2(D20T). This protein is similar to the one described in Example 10e, but contains a heavy chain derived from the γ4 rather than the γ2 IgG subclass. The fusion protein was expressed and purified essentially as described in Example 3.

h) dI-NHS76(γ4h)(FN>AQ)-ala-IL2(D20T). This protein, based on the protein of Example 10g, additionally contains the mutations that eliminate N-linked glycosylation in Fc and a potential T-cell epitope, as described in Example 10d. The fusion protein was expressed and purified essentially as described in Example 3. In one embodiment, fusion proteins of the invention include the heavy chain sequence of the dI-NHS76(γ4h)(FN>AQ) molecule fused to the IL-2(D20T) variant, depicted in SEQ ID NO: 37, and the light chain variable and constant region sequence corresponding to SEQ ID NO: 36. However, the heavy chain region of SEQ ID NO: 37 can be used in combination with any IgG light chain variable or constant region.

The Ig moiety of a fusion protein of the invention can include domains of heavy chain constant regions derived from any subclass of IgG, including combinations containing domains of IgG molecules derived from different species. Accordingly, the fusion proteins of the invention may include hinge regions derived from any subclass of IgG, for example, a hinge region derived from IgG gamma 1 (SEQ ID NO: 10), gamma 2 (SEQ ID 11) or gamma 4 (SEQ ID NO: 12).

Activity of Ig-IL2(D20T) variants in bioassays: The Ig-IL2(D20T) fusion proteins were tested in bioassays that measure the ability of cells dependent on IL-2 for growth to proliferate, which was expressed as an ED50 value (see Example 4). The assays were performed on murine CTLL-2 cells or human Kit-225 cells (which express IL-2Rαβγ), and human TF-1β cells or isolated murine NK cells (which express IL-2Rβγ).

For example, in a representative experiment it was found that, compared to huKS-ala-IL2, the ED50 value for dI-KS-ala-IL2(D20T) in IL-2Rαβγ bearing cells CTLL-2 was unchanged, whereas in IL-2Rβγ bearing cells TF-1β it was approximately 900-fold higher. The ED50 ratio, as defined in Example 4, therefore was around 150, revealing a shift of approximately 750-fold in selectivity towards IL-2Rαβγ bearing CTLL-2 cells as compared to huKS-ala-IL2. Compared to the shift in selectivity of approximately 20,000-fold (relative to KS-ala-IL2) seen with huKS-ala-IL2(N88R) in this pair of cell lines, the selectivity was reduced about 10 to 20-fold for dI-KS-ala-IL2(D20T), which reflected the measurable proliferative response obtained from IL-2Rβγ expressing cells. This trend was also apparent when human Kit 225 cells were used. As was found with other Ig-fusion proteins containing the KS antibody, deglycosylation of the antibody portion had a small but consistent effect on reducing the activity of the fusion protein in IL-2Rαβ expressing cells.

IL-2 dependent cell proliferation was also measured in Ig-IL(D20T) variants containing a different antibody moiety. It was found that, compared to dI-NHS76(γ2)-ala-IL2, the ED50 value for dI-NHS76(γ2)-ala-IL2(D20T) in IL-2Rαβγ bearing cells Kit-225 was increased 3-fold, whereas in IL-2Rβγ bearing cells TF-1β it was increased approximately 230-fold. The resultant ED50 ratio of 350 was in the same range as was seen with dI-KS(γ4)(FN>AQ)-ala-IL2(D20T) and at least 10 fold less selective than huKS-ala-IL2(N88R). Representative results are shown in Table 4.

TABLE 4

| Protein | ED50 Ratio TF-1β/CTLL-2 | ED50 Ratio TF-1β/Kit-225 |
| --- | --- | --- |
| dI-KS-ala-IL2(D20T) | 150 | 3000 |
| dI-KS(γ4) (FN > AQ)-ala-IL2(D20T) | | 5600* |
| dI-NHS76(γ2)-ala-IL2(D20T) | | 350 |

*= average of different lots

Pharmacokinetics of Ig-IL2(D20T) variants: To assess the interaction of Ig-IL2 variants with cell surface Fc receptors, binding of the Ig-IL2 fusion proteins to FcγR receptors was assayed in a cell-based ELISA, using U937 cells. Fusion proteins (huKS-ala-IL2, dI-huKS-ala-IL2, dI-KS-ala-IL2 (D20T), and dI-KS(γ4h)(FN>AQ)-ala-IL2(D20T)) were diluted 2-fold over a range from 100 μg/ml to 780 ng/ml, incubated with the cells and binding was detected using FITC-conjugated antihuman IgG Fc Ab F(ab')$_2$ (Jackson ImmunoResearch, West Grove, Pa.). The concentration of half-maximal binding of huKS-ala-IL2 and dI-KS-ala-IL2 for these cells was around 5 μg/ml, and interestingly, was increased two-fold with dI-KS-ala-IL2(D20T) protein. While the introduction of the mutation that prevents glycosylation of the Ig moiety (dI-KS(γ4h)(FN>AQ)-ala-IL2 (D20T)) reduced the binding of this protein to U973 cells 5- to 10-fold, binding was not completely abrogated.

The pharmacokinetic properties of the Ig-IL2(D20T) variants in mice were investigated, essentially as described in Example 5. Surprisingly, when compared to dI-KS-ala-IL2, the half-life of dI-KS-ala-IL2(D20T) was drastically reduced. Analysis of the PK profile indicated that the effect was particularly dramatic during the α-phase: whereas 50% of dI-KS-ala-IL2 was still available after 1 hour, only approximately 5% of dI-KS-ala-IL2(D20T) was still present. The slopes of the β-phase of the PK profile for these proteins were similar. An essentially identical PK profile to the one seen with dI-KS-ala-IL2(D20T) was obtained with the fusion protein dI-NHS76(γ2h)-ala-IL2(D20T), which contains an IgG of subclass γ2, that normally exhibits the least FcR binding affinity. Thus, the effect of the IL(D20T) protein moiety on the fusion protein was not limited to the antibody dI-KS.

Deglycosylation of an Ig fusion protein generally was observed to have the effect of enhancing the α-phase of a PK profile. The effect of enzymatic deglycosylation of dI-KS-ala-IL2(D20T) on the PK profile was therefore investigated. In fact, the α-phase of the PK profile was essentially restored to what had been observed with dI-KS-ala-IL2. The same effect was achieved when the glycosylation was abrogated by mutagenesis, as in the fusion protein dI-KS(γ4h) (FN>AQ)-ala-IL2(D20T). It is thus likely that the effect on the PK profile is due to reduced FcR binding.

Toxicity of Ig-IL2(D20T) variants: The toxicity of Ig-IL2 (D20T) variant KS(γ4h)(FN>AQ)-ala-IL2(D20T) was compared to that of dI-KS-ala-IL2 in Balb/C mice, as described in Example 6.

Both fusion proteins had a similar serum half-life in mice. dI-(γ4h)(FN>AQ)-ala-IL2(D20T) was administered in five daily doses of either 100 μg/mouse, 200 μg/mouse or 400 μg/mouse whereas dI-KS-ala-IL2 was administered in five daily doses of 40 μg/mouse. It was found that the mice survived even a dose of 400 μg/mouse of dI-KS(γ4h)

(FN>AQ)-ala-IL2(D20T), whereas control mice, which received one tenth the dose of dI-KS-ala-IL2, had died by day 6. The body weights of the mice treated with dI-KS(γ4h)(FN>AQ)-ala-IL2(D20T) was slightly affected, dropping transiently to 97% of initial weight on day 7. A difference of more than 10-fold in the tolerated dose may indicate a substantial improvement in the therapeutic index.

Efficacy of Ig-IL(D20T) variants for the treatment of tumors: The efficacy of Ig-IL2(D20T) variants was evaluated in Balb/C mice bearing a subcutaneous tumor derived from CT26/KSA cells, as described in Example 7a.

The fusion protein dI-KS(γ4h)(FN>AQ)-ala-IL2(D20T) was administered at doses of 15 μg/mouse and 30 μg/mouse. Tumors started at an average size of 126 mm$^3$ and reached sizes between 1800 mm$^3$ and 5000 mm$^3$ by day 28. Tumors in mice treated with 15 μg/mouse of dI-KS-ala-IL2 had grown to an average size of 355 mm$^3$, while tumors in mice treated with 15 μg/mouse of dI-KS-ala-IL2(D20T) had reached an average size of 2250 mm$^3$. This was most likely due to the poor PK of the molecule. Tumors in mice treated with dI-KS(γ4h)(FN>AQ)-ala-IL2(D20T) at the lower dose of 15 μg/mouse had grown to some extent, to an average size of 1450 mm$^3$; however, whereas at the 30 μg/mouse dose tumors reached an average size of 950 mm$^3$, significantly, in over half the mice the tumors had not grown appreciably. Thus, at increased doses dI-KS(γ4h)(FN>AQ)-ala-IL2(D20T) had a significant effect on inhibiting tumor growth. In fact, the dose used in this experiment was at least 12-fold lower than a maximal tolerated dose for this molecule and therefore it is likely to have an improved therapeutic index over the huKS-ala-IL2, which by comparison was administered at one third to one half of maximal tolerated dose.

Example 11

Relative Affinities of Wild-type and Mutant IL-2 Fusion Proteins for Different IL-2 Receptors Differential affinity of the various fusion proteins of the invention for an IL-2Rβγ receptor relative to an IL-2Rαβγ receptor can be measured by an assay such as a radioimmunoassay. Equal numbers of IL-2Rαβγ receptor expressing cells or IL-2Rβγ receptor expressing cells are plated on plastic plates. A dilution series is performed with an equal amount of either wild-type or mutant IL-2 fusion protein added to equal numbers of IL-2Rαβγ receptor expressing cells or IL-2Rβγ receptor expressing cells in order to obtain a standard curve. Unbound fusion proteins are washed away and the amount of fusion protein bound to each cell type is detected by a radiolabelled ligand. In the case of an Fc-IL-2 fusion protein, the ligand can be a molecule such as a staphylococcal protein A which binds to the Fc portion of an IgG. The ligand can also be another antibody that recognizes a portion of a particular subclass of the IgG molecule, for example, antibodies to IgG gamma 1, IgG gamma 2 or IgG gamma 4 constant regions. Unbound ligand is washed away and radioactivity of the plate containing either IL-2Rαβγ expresing cells bound with wild-type IL-2 fusion protein; IL-2αβγ expressing cells bound with mutant IL-2 fusion protein; IL-2Rβγ expressing cells bound with wild-type IL-2 fusion protein or IL-2Rβγ expressing cells bound with mutant fusion protein is measured on a gamma counter. The data obtained from the binding assay is normalized to account for the number of cells and receptors expressed on the cells.

In yet another assay, the fusion proteins themselves can be labeled, either radioactively, or non-radioactively using a variety of techniques well known in the art. Similar to the assay described above for a labeled ligand, either wild-type or mutant labeled fusion protein is added to equal number of plated cells and the amount of labeled fusion protein is measured.

The binding affinity of a fusion protein for a particular receptor is measured by the ratio of the concentration of the bound ligand or bound fusion protein, as described above, to the product of the concentration of unbound ligand or unbound fusion protein and the total concentration of the fusion protein added to each reaction. When compared to a wild-type IL-2 fusion protein, certain mutations in the IL-2 moiety alter the fusion protein's relative affinity for an IL-2Rβγ receptor and an IL-2Rαβγ receptor.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

All patents, patent applications and scientific publications referenced to herein are incorporated by reference in their entirety.

The invention claimed is:

1. A fusion protein comprising a non-IL-2 moiety fused to a mutant IL-2 moiety wherein the mutant IL-2 moiety comprises an amino acid substitution changing an aspartic acid to a threonine corresponding to position 20 of a mature human IL-2 protein consisting of the amino acid sequence set forth in SEQ ID NO:3, wherein the fusion protein exhibits greater selectivity than a reference protein towards cells expressing a high-affinity receptor, wherein said reference protein comprises the non-IL-2 moiety fused to a non-mutant IL-2 moiety, and
wherein said selectivity is measured as a ratio of activation of cells expressing IL-2Rαβγ receptor relative to activation of cells expressing IL-2Rβγ receptor.

2. The fusion protein of claim 1, wherein said selectivity is between about 0.1% to about 100% of selectivity of a protein, the protein comprising the non-IL-2 moiety fused to a mutant human IL-2 moiety, the mutant human IL-2 moiety comprising an asparagine to arginine amino acid substitution corresponding to position 88 of the mature human IL-2 protein consisting of the amino acid sequence set forth in SEQ ID NO:3.

3. The fusion protein of claim 1, wherein said selectivity is between about 0.1% to about 30% of selectivity of a protein, the protein comprising the non-IL-2 moiety fused to a mutant human IL-2 moiety, the mutant human IL-2 moiety comprising an asparagine to arginine amino acid substitution corresponding to position 88 of the mature human IL-2 protein consisting of the amino acid sequence set forth in SEQ ID NO:3.

4. The fusion protein of claim 1, wherein said selectivity is between about 1% to about 20% of selectivity of a protein, the protein comprising the non-IL-2 moiety fused to a mutant human IL-2 moiety, the mutant human IL-2 moiety comprising an asparagine to arginine amino acid substitution corresponding to position 88 of the mature human IL-2 protein consisting of the amino acid sequence set forth in SEQ ID NO:3.

5. The fusion protein of claim 1, wherein said selectivity is between about 2% to about 10% of selectivity of a protein, the protein comprising the non-IL-2 moiety fused to a mutant human IL-2 moiety, the mutant human IL-2 moiety comprising an asparagine to arginine amino acid substitution corresponding to position 88 of the mature human IL-2 protein consisting of the amino acid sequence set forth in SEQ ID NO:3.

6. The fusion protein of claim 1, wherein the cells expressing IL-2Rαβγ receptor are selected from the group consisting of CTLL-2, Kit 225 and mature T-cells.

7. The fusion protein of claim 1, wherein the cells expressing IL-2Rβγ receptor are selected from the group consisting of TF-1β cells and NK cells.

8. The fusion protein of claim 1, wherein said fusion protein has a longer serum half-life than mature human IL-2 protein.

9. The fusion protein of claim 1, wherein said non-IL-2 moiety is albumin.

10. The fusion protein of claim 1, wherein said non-IL-2 moiety comprises an antibody.

11. The fusion protein of claim 10, wherein the fusion protein comprises an amino acid sequence selected from the group consisting of the amino acid sequences set forth in SEQ ID NO:32, SEQ ID NO:35, and SEQ ID NQ:37.

12. The fusion protein of claim 1, wherein said mutant IL-2 moiety further comprises an amino acid substitution changing an asparagine to arginine corresponding to position 88 of the mature human IL-2 protein consisting of the amino acid sequence set forth in SEQ ID NO:3.

13. The fusion protein of claim 12, wherein said mutant IL-2 moiety further comprises an amino acid substitution changing a leucine to a threonine at position 85 and an amino acid substitution changing an isoleucine to a threonine corresponding to position 86 of the mature human IL-2 protein consisting of the amino acid sequence set forth in SEQ ID NO:3.

14. The fusion protein of claim 1, wherein said mutant IL-2 moiety further comprises a mutation corresponding to an amino acid position of mature human IL-2 protein consisting of the amino acid sequence set forth in SEQ ID NO:3, the amino acid position selected from the group consisting of lysine 8, glutamine 13, glutamic acid 15, histidine 16, leucine 19, glutamine 22, methionine 23, asparagine 26, phenylalanine 42, histidine 79, leucine 80, arginine at 81, aspartic acid 84, asparagine 88, isoleucine 92 and glutamic acid 95.

15. The fusion protein of claim 1, wherein said mutant IL-2 moiety further comprises mature human IL-2 protein with a mutation corresponding to an amino acid position of mature human IL-2 protein consisting of the amino acid sequence set forth in SEQ ID NO:3, the amino acid position selected from the group consisting of leucine 25, asparagine 31, leucine 40, methionine 46, lysine 48, lysine 49, threonine 51, aspartic acid 109, glutamic acid 110, alanine 112, threonine 113, valine 115, glutamic acid 116, asparagine 119, arginine 120, isoleucine 122, threonine 123, glutamine 126, serine 127, serine 130 and threonine 131.

16. The fusion protein of claim 15, wherein the amino acid mutation is an amino acid substitution changing a glutamine to an aspartic acid corresponding to position 126 of the mature human IL-2 protein consisting of the amino acid sequence set forth in SEQ ID NO:3.

17. The fusion protein of claim 1, wherein the non-IL-2 moiety comprises an antibody constant domain.

18. The fusion protein of claim 17, wherein said antibody constant domain comprises an IgG gamma-1 constant domain, an IgG gamma-2 constant domain or an IgG gamma-4 constant domain.

19. The fusion protein of claim 17, wherein said antibody constant domain comprises a mutation.

20. The fusion protein of claim 19, wherein said antibody constant domain comprises the amino acid sequence set forth in SEQ ID NO: 1, but wherein said mutation changes the asparagine of SEQ ID NO: 1 to a different amino acid.

21. The fusion protein of claim 20, wherein said asparagine is changed to a glutamine.

22. The fusion protein of claim 19, wherein said antibody constant domain comprises the amino acid sequence set forth in SEQ ID NO:2, but wherein said mutations changes the phenylalanine of SEQ ID NO:2 to an alanine and changes the asparagine of SEQ ID NO:2 to glutamine.

23. The fusion protein of claim 10, wherein the fusion protein comprises two peptides comprising amino acid sequences of SEQ ID NO: 35 and SEQ ID NO: 36.

\* \* \* \* \*

UNITED STATES PATENT AND TRADEMARK OFFICE
CERTIFICATE OF CORRECTION

PATENT NO. : 7,186,804 B2
APPLICATION NO. : 10/310719
DATED : March 6, 2007
INVENTOR(S) : Gilles et al.

It is certified that error appears in the above-identified patent and that said Letters Patent is hereby corrected as shown below:

Claim 22, at column 62, line 9, after the word "said", delete the word "mutations" and replace it with the word --mutation--.

Signed and Sealed this

First Day of May, 2007

JON W. DUDAS
*Director of the United States Patent and Trademark Office*

SEQUENCE LISTING

<160> NUMBER OF SEQ ID NOS: 37

<210> SEQ ID NO 1
<211> LENGTH: 7
<212> TYPE: PRT
<213> ORGANISM: Artificial Sequence
<220> FEATURE:
<223> OTHER INFORMATION: IgG gamma 1 sequence

<400> SEQUENCE: 1

Gln Tyr Asn Ser Thr Tyr Arg
1               5

```
<210> SEQ ID NO 2
<211> LENGTH: 5
<212> TYPE: PRT
<213> ORGANISM: Artificial Sequence
<220> FEATURE:
<223> OTHER INFORMATION: Ig Gamma 2 or 4 sequence

<400> SEQUENCE: 2

Gln Phe Asn Ser Thr
1               5

<210> SEQ ID NO 3
<211> LENGTH: 133
<212> TYPE: PRT
<213> ORGANISM: Homo sapiens

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 4
<211> LENGTH: 12
<212> TYPE: DNA
<213> ORGANISM: Artificial Sequence
<220> FEATURE:
<223> OTHER INFORMATION: Xma I site created in the human gamma-1 heavy
      chain gene

<400> SEQUENCE: 4
tccccgggta aa                                                              12

<210> SEQ ID NO 5
<211> LENGTH: 7
<212> TYPE: PRT
<213> ORGANISM: Artificial Sequence
<220> FEATURE:
<223> OTHER INFORMATION: wild-type huKS-ala-lL2 junction

<400> SEQUENCE: 5

Ser Pro Gly Lys Ala Pro Thr
1               5

<210> SEQ ID NO 6
<211> LENGTH: 7
<212> TYPE: PRT
<213> ORGANISM: Artificial Sequence
```

```
<220> FEATURE:
<223> OTHER INFORMATION: mutant huKS-ala-IL2 junction

<400> SEQUENCE: 6

Ser Gly Pro Ala Ala Pro Thr
1               5

<210> SEQ ID NO 7
<211> LENGTH: 327
<212> TYPE: PRT
<213> ORGANISM: Homo sapiens
<220> FEATURE:
<221> NAME/KEY: misc
<222> LOCATION: (1)..(327)
<223> OTHER INFORMATION: Human gamma 4 constant region

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

```
Leu Ser Leu Ser Leu Gly Lys
            325

<210> SEQ ID NO 8
<211> LENGTH: 330
<212> TYPE: PRT
<213> ORGANISM: Homo sapiens
<220> FEATURE:
<221> NAME/KEY: misc
<222> LOCATION: (1)..(330)
<223> OTHER INFORMATION: IgG1 constant region

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 9
<211> LENGTH: 326
<212> TYPE: PRT
<213> ORGANISM: Homo sapiens
<220> FEATURE:
<221> NAME/KEY: misc
<222> LOCATION: (1)..(326)
<223> OTHER INFORMATION: Human gamma 2 constant region

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 10
<211> LENGTH: 14
<212> TYPE: PRT
```

```
<213> ORGANISM: Artificial Sequence
<220> FEATURE:
<223> OTHER INFORMATION: Human IgG gamma 1 hinge region

<400> SEQUENCE: 10

Glu Pro Lys Ser Cys Asp Lys Thr His Thr Cys Pro Pro Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Human IgG gamma 2 hinge region

<400> SEQUENCE: 11

Glu Arg Lys Cys Cys Val Glu Cys Pro Pro Cys Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Human IgG gamma 4 hinge region

<400> SEQUENCE: 12

Glu Ser Lys Tyr Gly Pro Pro Cys Pro Ser Cys Pro
1               5                   10

<210> SEQ ID NO 13
<211> LENGTH: 9
<212> TYPE: PRT
<213> ORGANISM: Artificial
<220> FEATURE:
<223> OTHER INFORMATION: C-terminal of Ig G gamma 1 and gamma 2 constant
      regions

<400> SEQUENCE: 13

Lys Ser Leu Ser Leu Ser Pro Gly Lys
1               5

<210> SEQ ID NO 14
<211> LENGTH: 9
<212> TYPE: PRT
<213> ORGANISM: Artificial
<220> FEATURE:
<223> OTHER INFORMATION: C-terminal of IgG gamma 4 constant region

<400> SEQUENCE: 14

Lys Ser Leu Ser Leu Ser Leu Gly Lys
1               5

<210> SEQ ID NO 15
<211> LENGTH: 9
<212> TYPE: PRT
<213> ORGANISM: Artificial
<220> FEATURE:
<223> OTHER INFORMATION: mutated C-terminal of IgG gamma constant
      regions

<400> SEQUENCE: 15

Lys Ser Ala Thr Ala Thr Pro Gly Ala
1               5

<210> SEQ ID NO 16
<211> LENGTH: 32
```

```
<212> TYPE: DNA
<213> ORGANISM: Artificial Sequence
<220> FEATURE:
<223> OTHER INFORMATION: sense primer for generating huKS-ala-IL2 (N88R)
      fusion protein

<400> SEQUENCE: 16
ccccgggtgc cgcccaact tcaagttcta ca                                   32

<210> SEQ ID NO 17
<211> LENGTH: 53
<212> TYPE: DNA
<213> ORGANISM: Artificial Sequence
<220> FEATURE:
<223> OTHER INFORMATION: antisense primer for generating the huKS-ala-
      IL2(N88R) fusion protein

<400> SEQUENCE: 17
agccctttag ttccagaact attacgttga tcctgctgat taagtcccta ggt           53

<210> SEQ ID NO 18
<211> LENGTH: 40
<212> TYPE: DNA
<213> ORGANISM: Artificial Sequence
<220> FEATURE:
<223> OTHER INFORMATION: second sense primer

<400> SEQUENCE: 18
agttctggaa ctaaagggct ccgaaacaac attcatgtgt                          40

<210> SEQ ID NO 19
<211> LENGTH: 4
<212> TYPE: PRT
<213> ORGANISM: Artificial Sequence
<220> FEATURE:
<223> OTHER INFORMATION: mutant sequence in huKS M1 IL-2 variant

<400> SEQUENCE: 19

Thr Thr Ser Arg
1

<210> SEQ ID NO 20
<211> LENGTH: 12
<212> TYPE: PRT
<213> ORGANISM: Artificial Sequence
<220> FEATURE:
<223> OTHER INFORMATION: antibody-IL-2 junction sequence

<400> SEQUENCE: 20

Lys Ser Leu Ser Leu Ser Pro Gly Ala Ala Pro Thr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: mutant antibody-IL-2 junction sequence

<400> SEQUENCE: 21

Lys Ser Ala Thr Ala Thr Pro Gly Ala Ala Pro Thr
1               5                   10

<210> SEQ ID NO 22
<211> LENGTH: 6
<212> TYPE: PRT
<213> ORGANISM: Artificial Sequence
```

```
<220> FEATURE:
<223> OTHER INFORMATION: sequence in huKS M1-IL2 variant

<400> SEQUENCE: 22

Asp Leu Ile Ser Asn Ile
1               5

<210> SEQ ID NO 23
<211> LENGTH: 6
<212> TYPE: PRT
<213> ORGANISM: Artificial Sequence
<220> FEATURE:
<223> OTHER INFORMATION: mutant sequence in huKS M1-IL2 variant

<400> SEQUENCE: 23

Asp Thr Thr Ser Arg Ile
1               5

<210> SEQ ID NO 24
<211> LENGTH: 43
<212> TYPE: DNA
<213> ORGANISM: Artificial Sequence
<220> FEATURE:
<223> OTHER INFORMATION: sense primer for generating the N88R mutation

<400> SEQUENCE: 24
acttaagacc tagggacacc accagcagga tcaacgtaat agt                     43

<210> SEQ ID NO 25
<211> LENGTH: 18
<212> TYPE: DNA
<213> ORGANISM: Artificial Sequence
<220> FEATURE:
<223> OTHER INFORMATION: antisense primer for N88R mutation

<400> SEQUENCE: 25
atcatgtctg gatccctc                                                 18

<210> SEQ ID NO 26
<211> LENGTH: 7
<212> TYPE: PRT
<213> ORGANISM: Artificial Sequence
<220> FEATURE:
<223> OTHER INFORMATION: N to Q mutation in the CH2 domain of the Fc
      gamma 1 constant region

<400> SEQUENCE: 26

Gln Tyr Gln Ser Thr Tyr Arg
1               5

<210> SEQ ID NO 27
<211> LENGTH: 5
<212> TYPE: PRT
<213> ORGANISM: Artificial Sequence
<220> FEATURE:
<223> OTHER INFORMATION: FN to AQ mutation in Fc portion of gamma 2 or
      4 constant regions

<400> SEQUENCE: 27

Gln Ala Gln Ser Thr
1               5

<210> SEQ ID NO 28
<211> LENGTH: 48
<212> TYPE: DNA
<213> ORGANISM: Artificial Sequence
<220> FEATURE:
```

-continued

```
<223> OTHER INFORMATION: sense primer for D20T mutation

<400> SEQUENCE: 28
cagctgcaac tggagcatct cctgctgacc ctccagatga ttctgaat        48

<210> SEQ ID NO 29
<211> LENGTH: 20
<212> TYPE: DNA
<213> ORGANISM: Artificial Sequence
<220> FEATURE:
<223> OTHER INFORMATION: antisense primer for D20T mutation

<400> SEQUENCE: 29
attaaccctc actaaaggga                                       20

<210> SEQ ID NO 30
<211> LENGTH: 116
<212> TYPE: PRT
<213> ORGANISM: Artificial Sequence
<220> FEATURE:
<223> OTHER INFORMATION: hu-KS heavy chain variable region

<400> SEQUENCE: 30
```

Gln Ile Gln Leu Val Gln Ser Gly Ala Glu Val Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Thr Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Thr Ser Thr Ala Phe
65                  70                  75                  80

Leu Gln Ile Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Ser Val
            100                 105                 110

Thr Val Ser Ser
        115

```
<210> SEQ ID NO 31
<211> LENGTH: 106
<212> TYPE: PRT
<213> ORGANISM: Artificial Sequence
<220> FEATURE:
<223> OTHER INFORMATION: hu-KS light chain variable region

<400> SEQUENCE: 31
```

Glu Ile Val Leu Thr Gln Ser Pro Ala Thr Leu Ser Leu Ser Pro Gly
1               5                   10                  15

Glu Arg Val Thr Leu Thr Cys Ser Ala Ser Ser Ser Val Ser Tyr Met
            20                  25                  30

Leu Trp Tyr Gln Gln Lys Pro Gly Ser Ser Pro Lys Pro Trp Ile Phe
        35                  40                  45

Asp Thr Ser Asn Leu Ala Ser Gly Phe Pro Ala Arg Phe Ser Gly Ser
    50                  55                  60

Gly Ser Gly Thr Ser Tyr Ser Leu Ile Ile Ser Ser Met Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Leu Glu Ile Lys
            100                 105

<210> SEQ ID NO 32
<211> LENGTH: 579
<212> TYPE: PRT
<213> ORGANISM: Artificial Sequence
<220> FEATURE:
<223> OTHER INFORMATION: dI-KS-ala IL2 (D20T) heavy chain fused to
      IL-2 variant

<400> SEQUENCE: 32

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Ile Thr Ala Glu Thr Ser Thr Ser Thr Leu Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro

```
                340                 345                 350
Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
        420                 425                 430

Asn His Tyr Thr Gln Lys Ser Ala Thr Ala Thr Pro Gly Ala Ala Pro
        435                 440                 445

Thr Ser Ser Ser Thr Lys Lys Thr Gln Leu Gln Leu Glu His Leu Leu
        450                 455                 460

Leu Thr Leu Gln Met Ile Leu Asn Gly Ile Asn Asn Tyr Lys Asn Pro
465                 470                 475                 480

Lys Leu Thr Arg Met Leu Thr Phe Lys Phe Tyr Met Pro Lys Lys Ala
                485                 490                 495

Thr Glu Leu Lys His Leu Gln Cys Leu Glu Glu Glu Leu Lys Pro Leu
        500                 505                 510

Glu Glu Val Leu Asn Leu Ala Gln Ser Lys Asn Phe His Leu Arg Pro
        515                 520                 525

Arg Asp Leu Ile Ser Asn Ile Asn Val Ile Val Leu Glu Leu Lys Gly
530                 535                 540

Ser Glu Thr Thr Phe Met Cys Glu Tyr Ala Asp Glu Thr Ala Thr Ile
545                 550                 555                 560

Val Glu Phe Leu Asn Arg Trp Ile Thr Phe Cys Gln Ser Ile Ile Ser
                565                 570                 575

Thr Leu Thr

<210> SEQ ID NO 33
<211> LENGTH: 116
<212> TYPE: PRT
<213> ORGANISM: Artificial Sequence
<220> FEATURE:
<223> OTHER INFORMATION: dI-KS heavy chain variable region

<400> SEQUENCE: 33

Gln Ile Gln Leu Val Gln Ser Gly Pro Glu Leu Lys Lys Pro Gly Ser
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
        50                  55                  60

Lys Gly Arg Phe Thr Ile Thr Ala Glu Thr Ser Thr Ser Thr Leu Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
                100                 105                 110

Thr Val Ser Ser
            115
```

<210> SEQ ID NO 34
<211> LENGTH: 106
<212> TYPE: PRT
<213> ORGANISM: Artificial Sequence
<220> FEATURE:
<223> OTHER INFORMATION: dI-KS light chain variable region

<400> SEQUENCE: 34

```
Gln Ile Val Leu Thr Gln Ser Pro Ala Ser Leu Ala Val Ser Pro Gly
1               5                   10                  15

Gln Arg Ala Thr Ile Thr Cys Ser Ala Ser Ser Val Ser Tyr Ile
            20                  25                  30

Leu Trp Tyr Gln Gln Lys Pro Gly Gln Pro Pro Lys Pro Trp Ile Phe
        35                  40                  45

Asp Thr Ser Asn Leu Ala Ser Gly Phe Pro Ser Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105
```

<210> SEQ ID NO 35
<211> LENGTH: 580
<212> TYPE: PRT
<213> ORGANISM: Artificial Sequence
<220> FEATURE:
<223> OTHER INFORMATION: dI-NHS76(gamma2h)(FN>AQ)-ala-IL2(D20T) heavy
      chain fused to IL2 variant

<400> SEQUENCE: 35

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Lys Trp Ser Lys Phe Asp Tyr Trp Gly Gln Gly Thr Leu
            100                 105                 110

Val Thr Val Ser Ser Gly Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

-continued

```
Asn Phe Gly Thr Gln Thr Tyr Thr Cys Asn Val Asp His Lys Pro Ser
            195                 200                 205
Asn Thr Lys Val Asp Lys Thr Val Glu Pro Lys Ser Cys Asp Lys Thr
210                 215                 220
His Thr Cys Pro Pro Cys Pro Ala Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Asp Val Ser His Glu Asp Pro Glu
            260                 265                 270
Val Gln Phe Asn Trp Tyr Val Asp Gly Val Glu Val His Asn Ala Lys
            275                 280                 285
Thr Lys Pro Arg Glu Glu Gln Ala Gln Ser Thr Phe Arg Val Val Ser
290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Ala Thr Ala Thr Pro Gly Ala Ala
            435                 440                 445
Pro Thr Ser Ser Ser Thr Lys Lys Thr Gln Leu Gln Leu Glu His Leu
450                 455                 460
Leu Leu Thr Leu Gln Met Ile Leu Asn Gly Ile Asn Asn Tyr Lys Asn
465                 470                 475                 480
Pro Lys Leu Thr Arg Met Leu Thr Phe Lys Phe Tyr Met Pro Lys Lys
                485                 490                 495
Ala Thr Glu Leu Lys His Leu Gln Cys Leu Glu Glu Glu Leu Lys Pro
            500                 505                 510
Leu Glu Glu Val Leu Asn Leu Ala Gln Ser Lys Asn Phe His Leu Arg
            515                 520                 525
Pro Arg Asp Leu Ile Ser Asn Ile Asn Val Ile Val Leu Glu Leu Lys
530                 535                 540
Gly Ser Glu Thr Thr Phe Met Cys Glu Tyr Ala Asp Glu Thr Ala Thr
545                 550                 555                 560
Ile Val Glu Phe Leu Asn Arg Trp Ile Thr Phe Cys Gln Ser Ile Ile
                565                 570                 575
Ser Thr Leu Thr
            580

<210> SEQ ID NO 36
<211> LENGTH: 229
<212> TYPE: PRT
```

<213> ORGANISM: Artificial Sequence
<220> FEATURE:
<223> OTHER INFORMATION: dI-NHS76(gamma4th)(FN>AQ)-ala-IL2 (D20T)
      variable light chain region

<400> SEQUENCE: 36

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Val Thr Val Leu Gly Gly His Gln
            100                 105                 110

Asp Ser Asp Pro Leu Pro Leu Ile His Pro Ala Gly Gln Pro Lys Ala
        115                 120                 125

Ala Pro Ser Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
            180                 185                 190

Ser Tyr Leu Ser Leu Thr Pro Glu Gln Trp Lys Ser His Lys Ser Tyr
        195                 200                 205

Ser Cys Gln Val Thr His Glu Gly Ser Thr Val Glu Lys Thr Val Ala
    210                 215                 220

Pro Thr Glu Cys Ser
225

<210> SEQ ID NO 37
<211> LENGTH: 580
<212> TYPE: PRT
<213> ORGANISM: Artificial Sequence
<220> FEATURE:
<223> OTHER INFORMATION: dI-NHS76(gamma4h)(FN>AQ)-ala-IL2(D20T) heavy
      chain fused to IL-2 variant

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys

```
                85                  90                  95
Ala Arg Gly Lys Trp Ser Lys Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Cys Ser Arg Ser Thr Ser Glu Ser Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Pro Lys Ser Cys Asp Lys Thr His
                210                 215                 220

Thr Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Ala Gln Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Ile Phe Ser Cys Ser Val Met His Glu Ala Leu
                420                 425                 430

His Asn His Tyr Thr Gln Lys Ser Ala Thr Ala Thr Pro Gly Ala Ala
                435                 440                 445

Pro Thr Ser Ser Ser Thr Lys Lys Thr Gln Leu Gln Leu Glu His Leu
                450                 455                 460

Leu Leu Thr Leu Gln Met Ile Leu Asn Gly Ile Asn Asn Tyr Lys Asn
465                 470                 475                 480

Pro Lys Leu Thr Arg Met Leu Thr Phe Lys Phe Tyr Met Pro Lys Lys
                485                 490                 495

Ala Thr Glu Leu Lys His Leu Gln Cys Leu Glu Glu Glu Leu Lys Pro
                500                 505                 510
```

```
Leu Glu Glu Val Leu Asn Leu Ala Gln Ser Lys Asn Phe His Leu Arg
        515                 520                 525

Pro Arg Asp Leu Ile Ser Asn Ile Asn Val Ile Val Leu Glu Leu Lys
        530                 535                 540

Gly Ser Glu Thr Thr Phe Met Cys Glu Tyr Ala Asp Glu Thr Ala Thr
545                 550                 555                 560

Ile Val Glu Phe Leu Asn Arg Trp Ile Thr Phe Cys Gln Ser Ile Ile
            565                 570                 575

Ser Thr Leu Thr
            580
```